United States Patent
Grandi et al.

(10) Patent No.: US 11,427,625 B2
(45) Date of Patent: Aug. 30, 2022

(54) EXPRESSION OF NKG2D ACTIVATING LIGAND PROTEINS FOR SENSITIZING CANCER CELLS TO ATTACK BY CYTOTOXIC IMMUNE CELLS

(71) Applicant: University of Pittsburgh—Of the Commonwealth System of Higher Education, Pittsburgh, PA (US)

(72) Inventors: Paola Grandi, Cambridge, MA (US); Ndukaku Mgbechinyere Amankulor, Pittsburgh, PA (US); Joseph C. Glorioso, III, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 61 days.

(21) Appl. No.: 16/309,862

(22) PCT Filed: Jun. 14, 2017

(86) PCT No.: PCT/US2017/037531
§ 371 (c)(1),
(2) Date: Dec. 13, 2018

(87) PCT Pub. No.: WO2017/218689
PCT Pub. Date: Dec. 21, 2017

(65) Prior Publication Data
US 2020/0148742 A1 May 14, 2020

Related U.S. Application Data

(60) Provisional application No. 62/350,095, filed on Jun. 14, 2016.

(51) Int. Cl.
| A61K 48/00 | (2006.01) |
| C07K 14/74 | (2006.01) |
| A61P 35/00 | (2006.01) |
| C12N 15/85 | (2006.01) |

(52) U.S. Cl.
CPC ........ *C07K 14/70539* (2013.01); *A61P 35/00* (2018.01); *C12N 15/85* (2013.01); *C12N 2710/16632* (2013.01); *C12N 2710/16643* (2013.01); *C12N 2830/008* (2013.01)

(58) Field of Classification Search
CPC ... C07K 14/70539; A61P 35/00; C12N 15/85; C12N 2710/16632; C12N 2710/16643; C12N 2830/008
See application file for complete search history.

(56) References Cited

U.S. PATENT DOCUMENTS

| 6,653,447 B1 | 11/2003 | Cosman et al. |
| 8,129,167 B2 | 3/2012 | Cosman |
| 2013/0156808 A1 | 6/2013 | Jonjic |
| 2015/0165065 A1 | 6/2015 | Landgraf et al. |

FOREIGN PATENT DOCUMENTS

| WO | WO 2012/006181 A2 | 1/2012 |
| WO | WO 2015/066042 A1 | 5/2015 |

OTHER PUBLICATIONS

Engeland et al. ( Mol. Ther. (2014) 22(11):1949-59). (Year: 2014).*
Deng et al., "Antitumor immunity. A shed NKG2D ligand that promotes natural killer cell activation and tumor rejection," *Science*, 348(6230): 136-139 (2015).
European Patent Office, Extended European Search Report in European Application No. 17814031.5, dated Nov. 8, 2019.
Geisler, et al. "MicroRNA-regulated viral vectors for gene therapy," *World J. Exp Med.*, 6(2): 37-54 (2016).
Lanier, L. L., "NKG2D Receptor and Its Ligands in Host Defense," *Cancer Immunol. Res.*, 3(6): 575-582 (2015).
Zhang et al., "IDH mutant gliomas escape natural killer cell immune surveillance by downregulation of NKG2D ligand expression," *Neuro Oncol.*, 18(10): 1402-1412 (2016).
International Bureau, International Search Report and Written Opinion in International Application No. PCT/US2017/037531, dated Sep. 29, 2017.
Uchida et al., "A double mutation in glycoprotein gB compensates for ineffective gD-dependent initiation of herpes simplex virus type 1 infection," *J. Virol.*, 84(23): 12200-12209 (2010).
Varghese et al., "Oncolytic herpes simplex virus vectors for cancer virotherapy," *Cancer Gene Ther.*, 9: 967-978 (2002).
Zhang et al., "Abstract 3669: IDH mutant glial cell resistance to natural killer cell cytotoxicity," *Cancer Res.*, 74: 3669 (2014).
Verweij et al., "Viral inhibition of the transporter associated with antigen processing (TAP): a striking example of functional convergent evolution," *PLoS Pathog.*, 11(4): e1004743 (Apr. 2015).

* cited by examiner

*Primary Examiner* — J. E. Angell
(74) *Attorney, Agent, or Firm* — Leydig, Voit & Mayer

(57) ABSTRACT

Provided is a recombinant viral vector that expresses a NKG2D activating ligand, such as a UL-16 binding protein. When introduced into a cancer cell, the vector can cause expression of the NKG2D activating ligand, thereby overcoming repression of NK-mediated (or other effector cell, e.g., macrophage) cytotoxicity and causing effector cell-mediated death of the cancer cell. Expression of the NKG2D activating ligand can be controlled by a miRNA present in greater concentration in noncancerous cells than in cancer cells, which can permit selective expression of the ligand in cancer cells and reduced cytotoxicity toward noncancerous cells. The vector can cause expression of an oncolytic factor. When formulated into a pharmaceutical composition and administered to a patient, the vector can be used to treat cancer. The cancer can be a glioma, such as glioblastoma including one with an isocitrate dehydrogenase (IDH) mutation. The vector can be a herpes simplex virus vector, among others.

36 Claims, 27 Drawing Sheets

Specification includes a Sequence Listing.

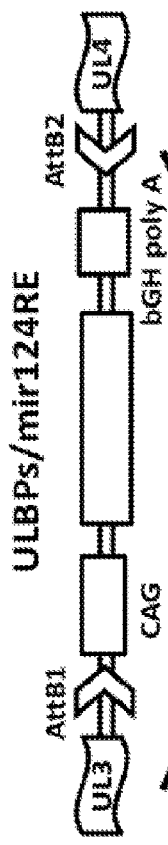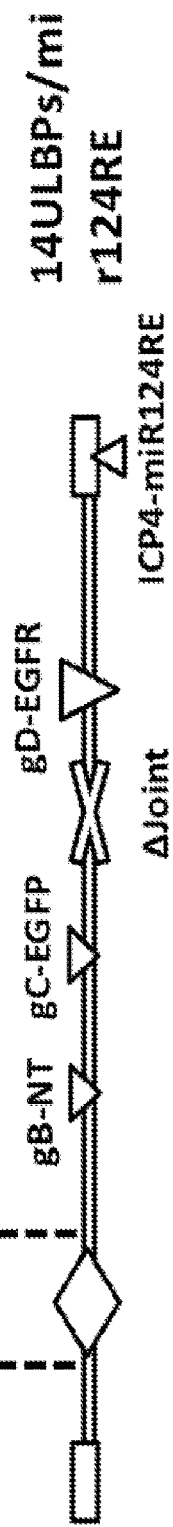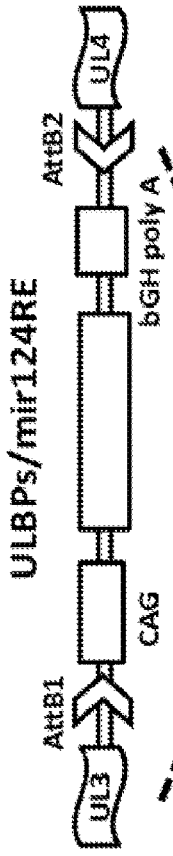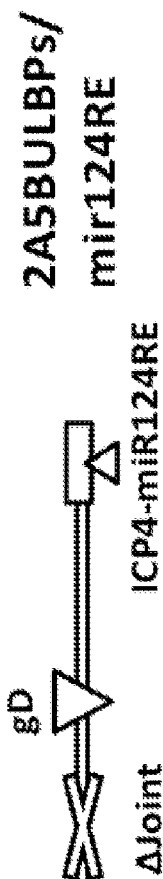
Fig. 12A
Fig. 12B

SEQUENCE LISTING

<160> NUMBER OF SEQ ID NOS: 2

<210> SEQ ID NO 1
<211> LENGTH: 906
<212> TYPE: DNA
<213> ORGANISM: Artificial Sequence
<220> FEATURE:
<223> OTHER INFORMATION: Synthetic sequence

<400> SEQUENCE: 1

| | | | | | | |
|---|---|---|---|---|---|---|
| atgtctgcac | ttctgatcct | agctcttgtt | ggagctgcag | ttgctgacta | caaagaccat | 60 |
| gacggtgatt | ataaagatca | tgacatcgat | tacaaggatg | acgatgacaa | gcttggctgg | 120 |
| tcccgggcag | gatgggtcga | cacacactgt | ctttgctatg | acttcatcat | cactcctaag | 180 |
| tccagacctg | aaccacagtg | gtgtgaagtt | caaggcctgg | tggatgaaag | gccttttctt | 240 |
| cactatgact | gtgttaacca | caaggccaaa | gcctttgctt | ctctggggaa | gaaagtcaat | 300 |
| gtcacaaaaa | cctgggaaga | acaaactgaa | acactaagag | acgtggtgga | tttccttaaa | 360 |
| gggcaactgc | ttgacattca | agtggagaat | ttaatacccA | ttgagcccct | caccctgcag | 420 |
| gccaggatgt | cttgtgagca | tgaagcccat | ggacacggca | gaggatcttg | gcagttcctc | 480 |
| ttcaatggac | agaagttcct | cctctttgac | tcaaacaaca | gaaagtggac | agcacttcat | 540 |
| cctggagcca | gaagatgac | agagaagtgg | gagaagaaca | gggatgtgac | catgttcttc | 600 |
| cagaagattt | cactggggga | ttgtaagatg | tggcttgaag | aatttttgat | gtactgggaa | 660 |
| caaatgctgg | atccaacaaa | accaccctct | ctggccccag | gcacaaccca | acccaaggcc | 720 |
| atggccacca | ccctcagtcc | ctggagcctt | ctcatcatct | tcctctgctt | cattctagct | 780 |
| ggcagatgag | aattcggcat | tcaccgcgtg | ccttatagta | ccagggcatt | caccgcgtgc | 840 |
| cttaaggatc | ctggcattca | ccgcgtgcct | taatgactgc | ggcattcacc | gcgtgcctta | 900 |
| agatct | | | | | | 906 |

<210> SEQ ID NO 2
<211> LENGTH: 900
<212> TYPE: DNA
<213> ORGANISM: Artificial Sequence
<220> FEATURE:
<223> OTHER INFORMATION: Synthetic sequence

<400> SEQUENCE: 2

| | | | | | | |
|---|---|---|---|---|---|---|
| atgtctgcac | ttctgatcct | agctcttgtt | ggagctgcag | ttgctgacta | caaagaccat | 60 |
| gacggtgatt | ataaagatca | tgacatcgat | tacaaggatg | acgatgacaa | gcttttcgac | 120 |
| tggtccggga | cggggcgggc | cgacgctcac | tctctctggt | ataacttcac | catcattcat | 180 |
| ttgcccagac | atgggcaaca | gtggtgtgag | gtccagagcc | aggtggatca | gaagaatttt | 240 |
| ctctcctatg | actgtggcag | tgacaaggtc | ttatctatgg | gtcacctaga | agagcagctg | 300 |
| tatgccacag | atgcctgggg | aaaacaactg | gaaatgctga | gagaggtggg | gcagaggctc | 360 |
| agactggaac | tggctgacac | tgagctggag | gatttcacac | ccagtggacc | cctcacgctg | 420 |
| caggtcagga | tgtcttgtga | gtgtgaagcc | gatggataca | ccgtggatc | ttggcagttc | 480 |
| agcttcgatg | gacggaagtt | cctcctcttt | gactcaaaca | acagaaagtg | gacagtggtt | 540 |
| cacgctggag | ccaggcggat | gaaagagaag | tgggagaagg | atagcggact | gaccaccttc | 600 |
| ttcaagatgg | tctcaatgag | agactgcaag | agctggctta | gggacttcct | gatgcacagg | 660 |
| aagaagaggc | tggaacccac | agcaccaccc | accatggccc | caggcttagc | tcaacccaaa | 720 |
| gccatagcca | ccaccctcag | tccctggagc | ttcctcatca | tcctctgctt | catcctccct | 780 |

```
ggcatctgag aattcggcat tcaccgcgtg ccttatagta ccagggcatt caccgcgtgc    840
cttaaggatc ctggcattca ccgcgtgcct taatgactgc ggcattcacc gcgtgcctta    900
```

EXPRESSION OF NKG2D ACTIVATING LIGAND PROTEINS FOR SENSITIZING CANCER CELLS TO ATTACK BY CYTOTOXIC IMMUNE CELLS

CROSS REFERENCE TO RELATED APPLICATIONS

This application is the United States National Phase application under 35 U.S.C. § 371 of International Patent Application PCT/US2017/037531, filed Jun. 14, 2017, and which claims the benefit of U.S. Provisional Patent Application 62/350,095, filed Jun. 14, 2016, the entire contents of each of which are incorporated herein by reference.

STATEMENT REGARDING FEDERALLY SPONSORED RESEARCH AND DEVELOPMENT

This invention was made with Government support under Grant Numbers AI175052 and CA163205 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,108 Byte ASCII (Text) file named "740992_ST25," created on Apr. 29, 2019.

BACKGROUND OF THE INVENTION

Methylation-related epigenetic repression is associated with the development of human malignancies. In particular, epigenetic repression of natural killer (NK) cell ligands is a common occurrence that co-evolves with cancer development. New techniques for overcoming repression of NK cell ligands can be of use in the treatment of cancer.

International PCT Publication No. WO 2015/066042 (incorporated herein by reference in its entirety) discloses recombinant oncolytic Herpes Simplex Virus (oHSV) expressing a transgenic ligand specific for a cell surface molecule and one or more copies of a microRNA target sequence inserted into a HSV replication locus. A review of Oncolytic HSV and methods of use is disclosed in Varghese and Rabkin, *Cancer Gene Therapy* (2002) 9, 967-978, also incorporated herein by reference.

BRIEF SUMMARY OF THE INVENTION

The present invention is based on the discovery that transcriptional repression of NKG2D activating ligands (NKG2DLs) in isocitrate dehydrogenase (IDH) mutant ($IDH^{Mut}$) gliomas, for example, correlate with decreased susceptibility of $IDH^{Mut}$ cells to natural killer (NK) cell-mediated cytolysis in vitro and ex vivo compared to IDH wild type (WT, $IDH^{WT}$) cells. The invention provides HSV-based vectors expressing human NKG2D ligands, such as UL16-Binding Proteins (ULBPs) (e.g., ULBP1-ULBP6, in particular ULBP1 and ULBP3), which, in some embodiments, can enhance NK and T cell recognition of cancer cells. Virus-mediated expression of ULBPs can result in activation of NK cell and/or T cells that recognize the ULBPs through the NKG2D receptor (NKG2DR) and subsequently destroy the target tumor cell. This strategy represents a new approach of vector-mediated gene therapy for treatment of cancer.

In some embodiments, the present invention provides a recombinant viral vector comprising one or more exogenous genes (e.g., transgenes) that express at least one NKG2D-activating ligand protein when the vector is introduced into a cancer cell. The vector can be, for example, an adenoviral, a retroviral, an adeno-associated viral, or a Herpes Simplex Virus (HSV) vector. The expression of the ligand protein can sensitize the cancer cell to effector cell-mediated cytotoxicity (e.g., NK cell-mediated cytotoxicity). The NKG2D ligand protein can be a UL16-Binding Protein (ULBP), such as any of ULBP1-ULBP6, MIC-A, or MIB-B. In specific embodiments, the ULBP is one or both of ULBP1 and ULBP3 such that the inventive vector expresses ULPB1, ULBP3 or both ULBP1 and ULBP3 when the vector is introduced into a cancer cell.

In some embodiments, the expression of the NKG2D ligand is under regulatory control of a cellular biomolecule. In some embodiments, the cellular biomolecule is present at a greater concentration in noncancerous cells than in cancerous cells such that the expression of the NKG2D ligand is down-regulated in the noncancerous cell relative to expression in the cancer cell. In some embodiments, the cellular biomolecule is a micro RNA (miRNA or miR). In some embodiments, the miR is one or more of miR122, miR124, miR128, miR137, and/or miR199. In some embodiments, the vectors described herein comprise one or miRNA target sequences inserted into one or more viral genes and/or one or more exogenous genes. In some embodiments, the vector comprises 2, 3, 4, 5, 6 or more target sequences inserted into one or more exogenous genes. In some embodiments, the miR target sequences are in tandem. In some embodiments, the miR target sequences are separated by spacers of four or more nucleotides. The one or more miRNA target sequences can be a reverse complement of the miRNA. In some embodiments, the one or more miRNA target sequences are inserted into the 3' untranslated region (UTR) of one or more viral genes and/or the exogenous gene that expresses the NKG2D ligand.

In some embodiments, the vector may comprise one or more gene knockouts, knockdowns, deletions, insertions or other mutations that impair or block replication of the vector and/or expression of toxic genes. For example, in one non-limiting illustrative embodiment, an HSV vector may comprise one or more gene knockouts, knockdowns, deletions, insertions or other mutations in one or more of the ICP0, ICP4, ICP22, ICP27 and/or ICP47 genes. In further embodiments, the HSV vector may comprise one or more gene knockouts, knockdowns, deletions, insertions or other mutations in all of the ICP0, ICP4, ICP22, ICP27 and ICP47 genes. In some embodiments, the vector is replication incompetent (i.e., does not replicate in non-complementing cells and/or in vivo).

In some embodiments, the recombinant viral vectors described herein are introduced into a cell. In some embodiments, the cell can be any cancer cell susceptible to NKG2D-dependent cytolysis by effector immune cells, including $IDH^{Mut}$ and $IDH^{WT}$ cancer cells.

In some embodiments, the vector comprises a first exogenous gene encoding at least one NKG2D-activating ligand protein and a second exogenous gene encoding an oncolytic factor. Non-limiting examples of oncolytic factors include enzymes (e.g., proteinases), cytokines, chemokines, antibodies, or other biologically active polypeptides. In certain embodiments, the oncolytic factor is an enzyme, such as a metalloproteinase (e.g., matrix metalloproteinase-9 (MMP-9)), a prodrug-converting enzyme, cytosine deaminase, thymidine kinase, purine nucleoside phosphorylase, or an enzyme selected from those listed in Table 1.

In some embodiments, the present invention provides a nucleic acid encoding any of the vectors described herein. In some embodiments, the nucleic acid may be a bacterial artificial chromosome (BAC). In some embodiments, the present invention provides a viral stock of any of the vectors described herein. In some embodiments, the present invention provides a pharmaceutical composition comprising any of the vectors described herein. In further embodiments, the pharmaceutical composition comprises a pharmaceutically acceptable carrier.

In some embodiments, the present invention provides a method for expressing a NKG2D ligand protein in a cancer cell comprising introducing any of the vectors, pharmaceutical compositions, or viral stocks described herein to the cancer cell under conditions sufficient for the vector to infect the cancer cell and to express the NKG2D ligand protein. In some embodiments, the cell may be derived from a subject suffering from a cancer (e.g., a primary cell sample, such as a biopsy). In some embodiments, the cancer cell may be, but is not limited to a glioma cell, such as a glioblastoma multiforme (GBM) cell. In such embodiments, expression of the NKG2D ligand protein increases susceptibly of the cancer cell (e.g., the glioblastoma cell) to NK-mediated cytoxicity.

In some embodiments, the present invention provides a method for treating a cancer in a mammalian subject in need thereof comprising administering any of the vectors, pharmaceutical compositions, or viral stocks described herein to the subject, thereby treating the cancer. In some embodiments, the vector, pharmaceutical composition, or stock may be administered directly to the tumor, e.g., by intratumoral injection, intracranial injection (as appropriate to the tumor type), or systemically.

BRIEF DESCRIPTION OF THE DRAWINGS

FIG. 1A: Unsupervised hierarchical clustering of 62 differentially expressed genes with p-values<1e$^{-7}$ and absolute difference in gene expression greater than 3. Markers are clustered by their expression values using a Pearson correlation as a distance measure. FIG. 1B: Gene expression analysis of other known NKG2D ligands from the same cohort as described in FIG. 1A. ULBP1 and ULBP3 exhibited significantly lower expression in IDH$^{Mut}$ compared to IDH$^{WT}$. FIG. 1C: Mean methylation values for 152 low-grade glioma patients (130 IDH$^{Mut}$; 32 IDH$^{WT}$) from the TCGA low-grade glioma database. (*=p<0.05; ***=p<0.001)

FIG. 2A: RT-PCR expression values comparing expression of NKG2DLs in IDH$^{Mut}$ or IDH$^{WT}$ immortalized human astrocyte cell lines. Data shown represents expression levels relative to 18s RNA. Results shown are representative of 3 independent experiments. FIG. 2B: Real time PCR expression for NKGD2Ls was performed on patient-derived IDH$^{Mut}$ or IDH$^{WT}$ primary glioma stem-like cells. Each data point represents primary glioma cells derived from an individual patient tumor. Data shown represent expression levels relative to 18s RNA. For FIGS. 2A and 2B, all samples were run in triplicates, and error bars show standard deviation among the replicates. (*=p<0.05; ***=p<0.001)

FIG. 3A: NK-mediated specific lysis of IDH$^{Mut}$ and parental astrocytes (PA) measured at three different effector target ratios (1:5, 1:10 and 1:20). Statistical differences in specific lysis of IDH$^{Mut}$ astrocytes (grey line, squares) and PA astrocytes (black line, circles) were measured using paired student t-tests. FIG. 3B: Specific lysis of patient-derived IDH$^{Mut}$ (black circles) or IDH$^{WT}$ (black squares) GSCs origin by NK-92 cells effector cells. FIGS. 3C and 3D: Elaboration of IFN-γ measured by ELISA in supernatants of experiments from FIGS. 3A and 3B, respectively. Differences in IFN-γ concentration were determined by paired student t-tests. (*=p<0.05; =p<0.01; *=p<0.001).

FIG. 4A: Donor-derived NK-mediated cytolysis of IDH$^{Mut}$ or IDH$^{WT}$ astrocytes was performed in the presence or absence of NKG2D blocking antibodies. Specific lysis was determined by 7-AAD flow cytometry. NK lysis of IDH$^{WT}$ astrocytes was markedly reduced in the presence of NKG2D blocking antibody (10.2% versus 3.03%; p=0.04), but no difference was seen with an isotype control antibody. IDH$^{Mut}$ astrocytes exhibited low levels of NK-mediated specific lysis (<2%), and no statistically significant change was seen upon NKG2D blockade. FIG. 4B: Cell-free supernatants from experiments in FIG. 4A were extracted for assessment of IFN-γ levels by ELISA. Data shown are representative of 3 independent experiments. Error bars represent SD between each sample. (*=p<0.05; =p<0.01; =p<0.001).

(FIG. 9C) Kaplan-Meier survival plot. Triturated primary glioma line GBM30 cells were implanted intracranially and PBS or JΔNI7-ULBP3 virus ($2\times10^9$ genome copies in 2.5 µl) were injected 7 days later at the same coordinates. Median survival: PBS=18.5 d, ULBP3=24.5 d.

FIG. 12A and FIG. 12B show vector diagrams of oncolytic HSV vectors that overexpress ULBPs and ULBPmir124RE (RE=response element). "USBPs" here refer to any ULBP, such as ULBP1, ULBP3, or others. The oncolytic vectors were created by recombination, replacing the gateway cassette in the 2A5BGw (2A5B=gD wt; gB-NT=virus entry enhancing double mutation in gB; gC-EGFP=fusion of the complete gC ORF to EGFP via a T2A sequence; Δjoint=deletion of the complete internal repeat region including one copy of ICP4; ICP4: mir124=insertion to T124 in the 3' UTR of the remaining ICP4 gene; or in 14Gw (in which the gD has been engineered to infect through the human EGFR or EGFRvIII and has the same modification listed in 2A5B) with the ULBP expression cassettes.

2A5B ULBP1, Clone #2
2A5B ULBP1mir124RE Clone #2 (FIG. 12B)
2A5B ULBP3 Clone #1
2A5B ULBP3mir124RE Clone #2 (FIG. 12B)
14 ULBP1 Clone #1
14 ULBP1mir124RE Clone #1 (FIG. 12A)
14 ULBP3 Clone #3
14 ULBP3mir124RE Clone #8 (FIG. 12A)

The 2A5B ULBP1 and 2A5B ULBP3 constructs are as represented in FIG. 12B without the ICP4-miR123RE modification, and the 14 ULBP1 and 14 ULBP3 constructs are as represented in FIG. 12B without the ICP4-miR123RE modification.

FIGS. 14-17 depict data concerning tropism vectors of the present invention. J/A, J/C, and J/EGFR cells were infected with of KMMP9, KGW or the parental virus KG4:T124 carrying a WT gD for 6 hours and immunostained with an antibody to ICP4 in order to detect virus entry. Entry of the EGFR-retargeted 14-ULBP construct through human EGFR was confirmed by infecting cells expressing either human EGFR receptor (J-EGFR) the HSV natural receptors HveA and Hve C (J/A and J/C cells; on the other end the non-retargeted vector (2A5B backbone) could inject only the J/A or J/C cells (transduced for expression of the natural receptors for gD).

Figure 18:
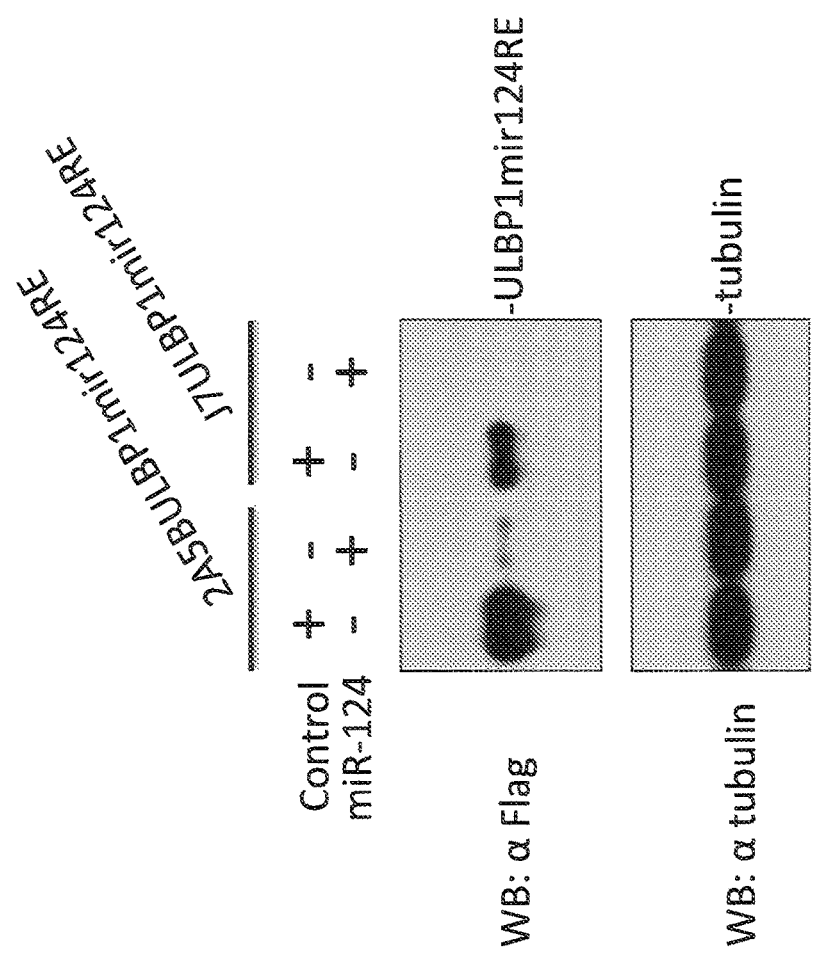

FIG. 18 shows down-regulation of Flag-tagged ULBP1 expression by miR124. 293T cells were transfected with miR124 or scramble control, using≅100 pmol (5 µL from a stock 20 µM). After 24 hours, cells were infected either with the oncolytic vector 2A5BULBP1mir124RE (See construct in FIG. 12B) or with the defective virus J7ULBP1mir124 at MOI 0.1. 24 h.p.i. cells were collected for WB (total 100 µL/sample—Load 2 µL).

Figure 19:
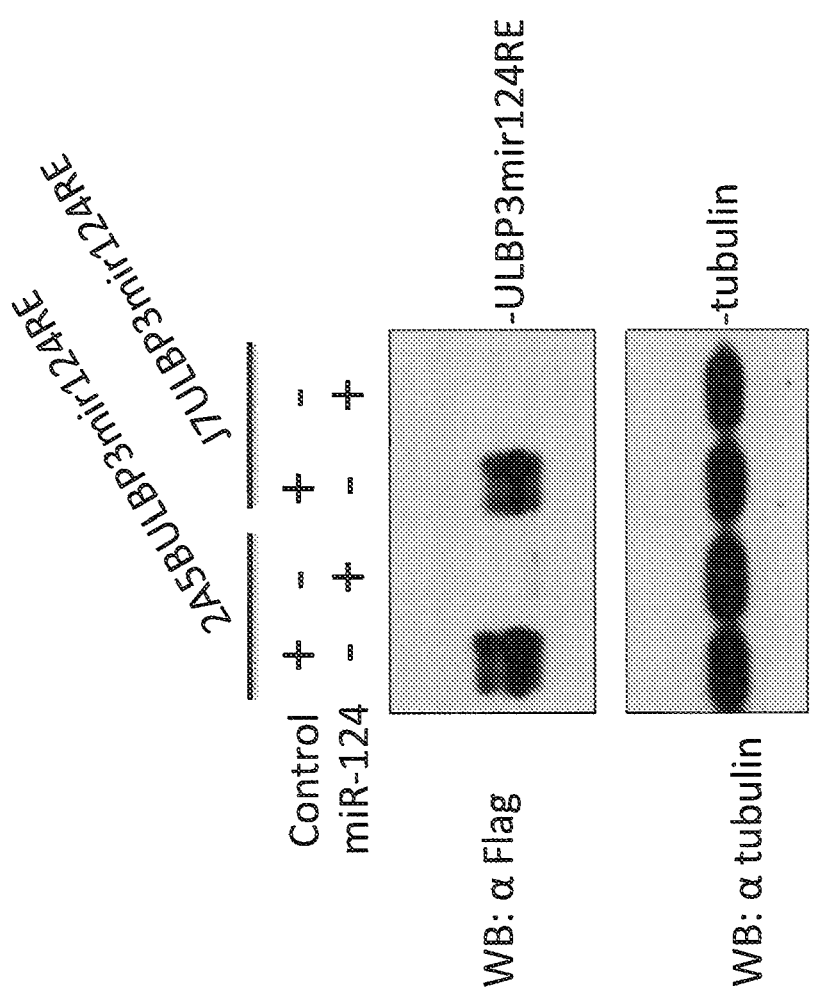

FIG. 19 depicts ULBP1 down-regulation by miR124. 293T cells were transfected with miR124 or scramble control (J7ULBP3mir124), using≅100 pmol (5 µL from a stock 20 µM). After 24 hours, cells were infected either with the oncolytic vector 2A5BULBP3mir124RE (See construct in FIG. 12B) or with the defective virus J7ULBP3mir124 at MOI of 0.1. 24 h.p.i. cells were collected for WB (total 100 µL/sample—Load 2 µL).

Figure 20:
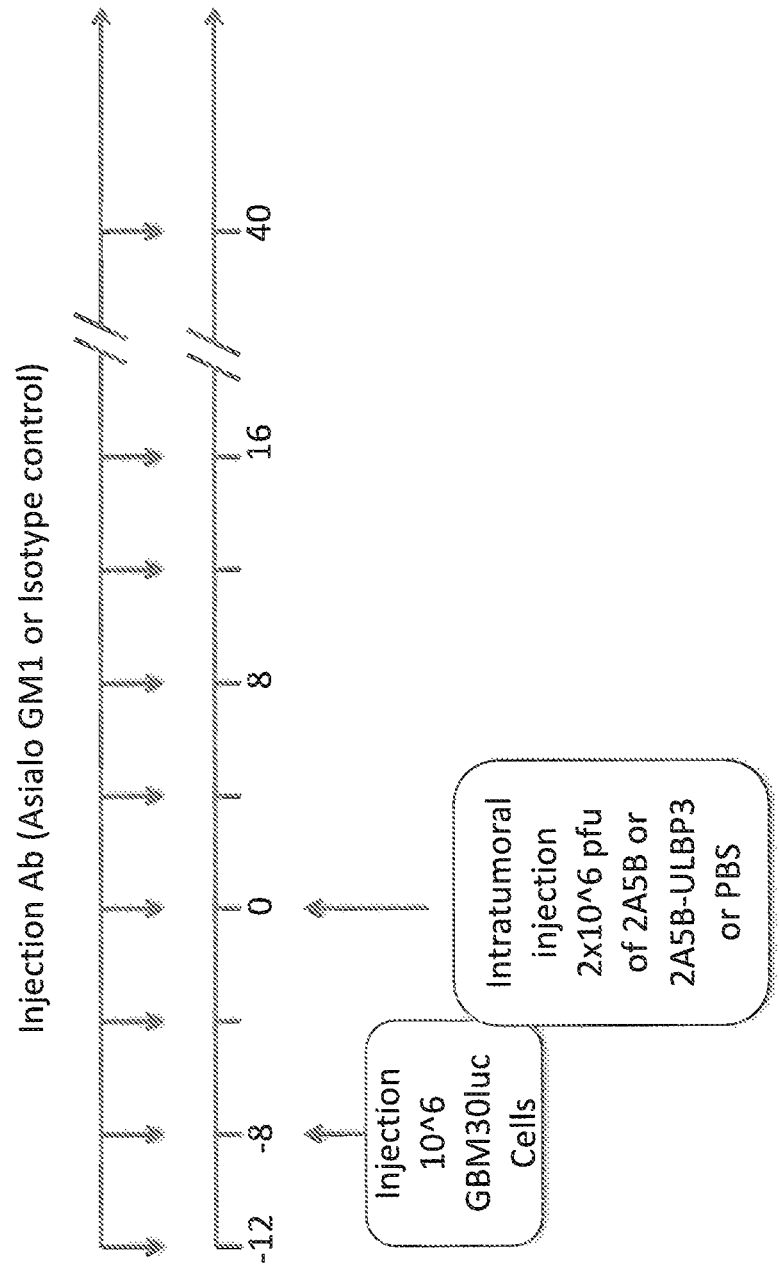

FIG. 20 depicts the experimental design of an experiment demonstrating that ULBP3 improves the therapeutic efficacy of 2A5B. The timeline depicted in FIG. 20 represents days; either Asialo GM1 Ab or isotype control were injected every four days, as depicted.

Figure 21:
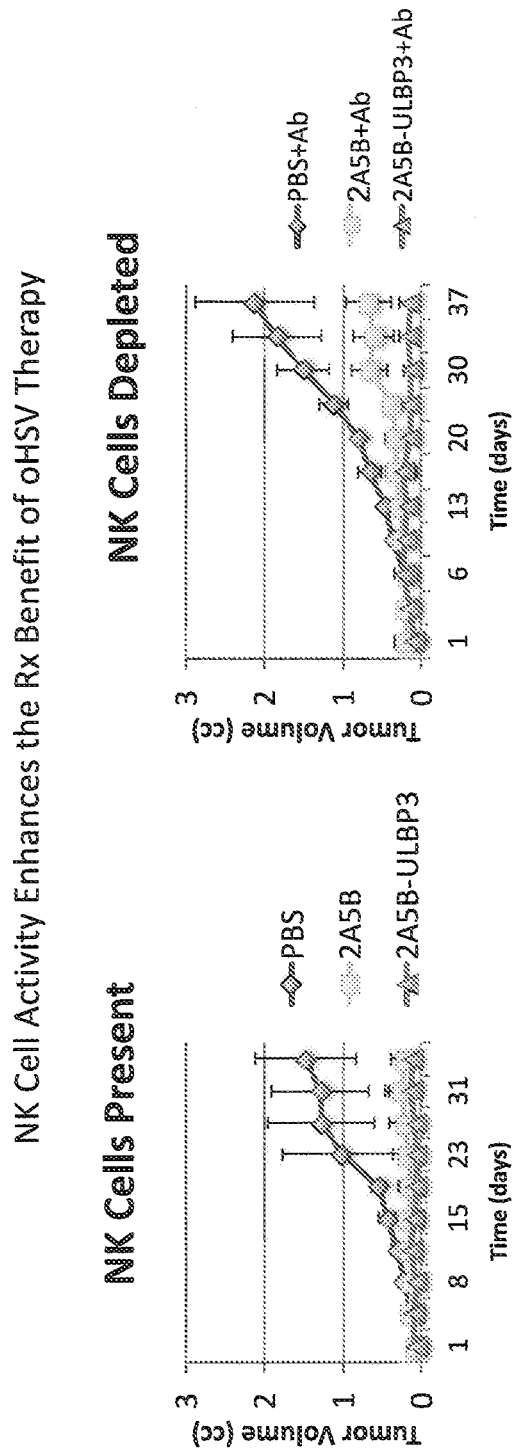

FIG. 21 graphically presents data demonstrating that ULBP3 improves the therapeutic efficacy of 2A5B both with NK cell present (left panel) and NK cells depleted (right panel).

Figure 22A:
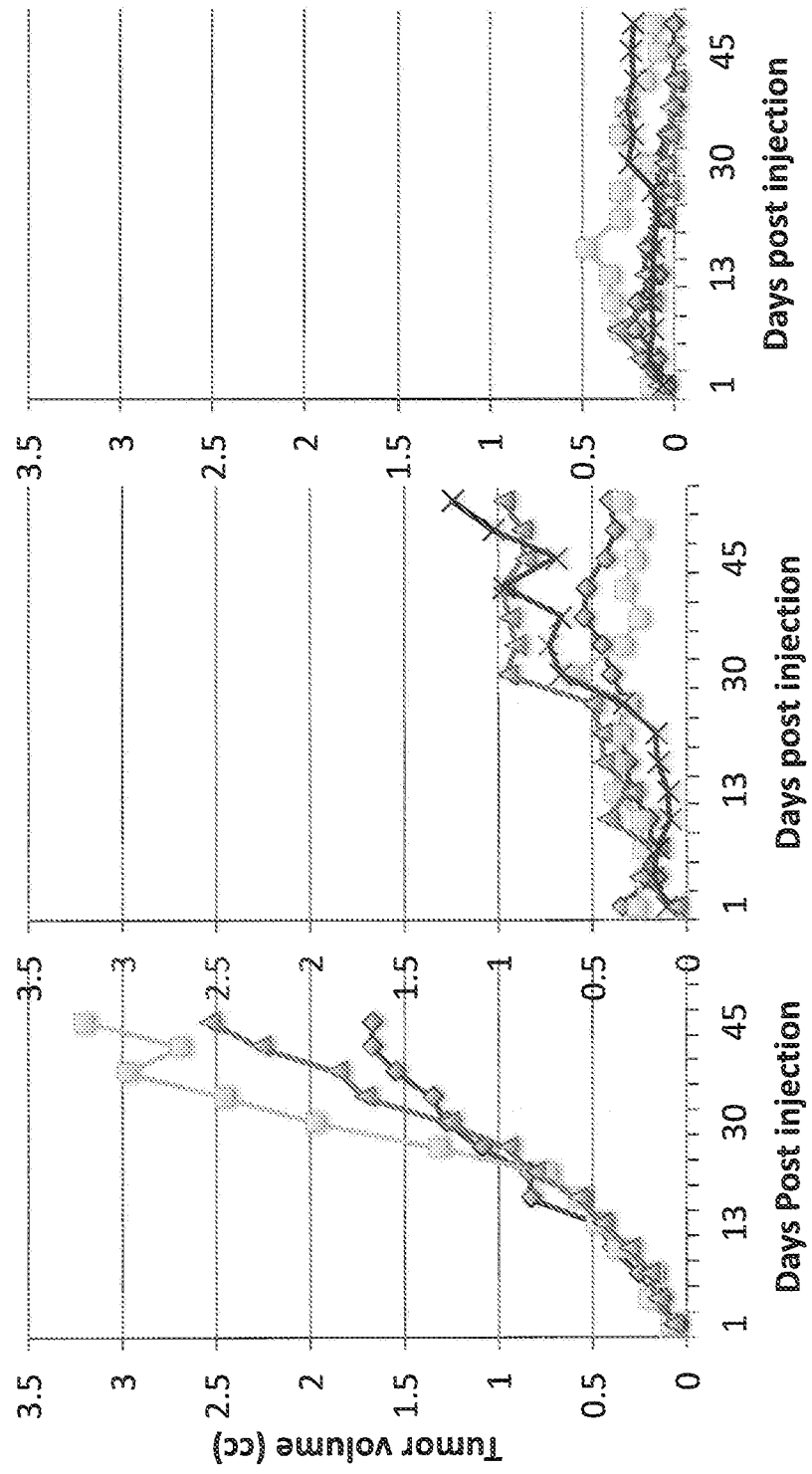

FIG. 22A presents data comparing the tumor suppressing ability of the oncolytic HSV vector, 2A5B ULBP3 (right panel), to the backbone vector (2A5B) (center panel) and also to sham (PBS)-treated animals (left column), each in the absence of NK cells.

Figure 22B:
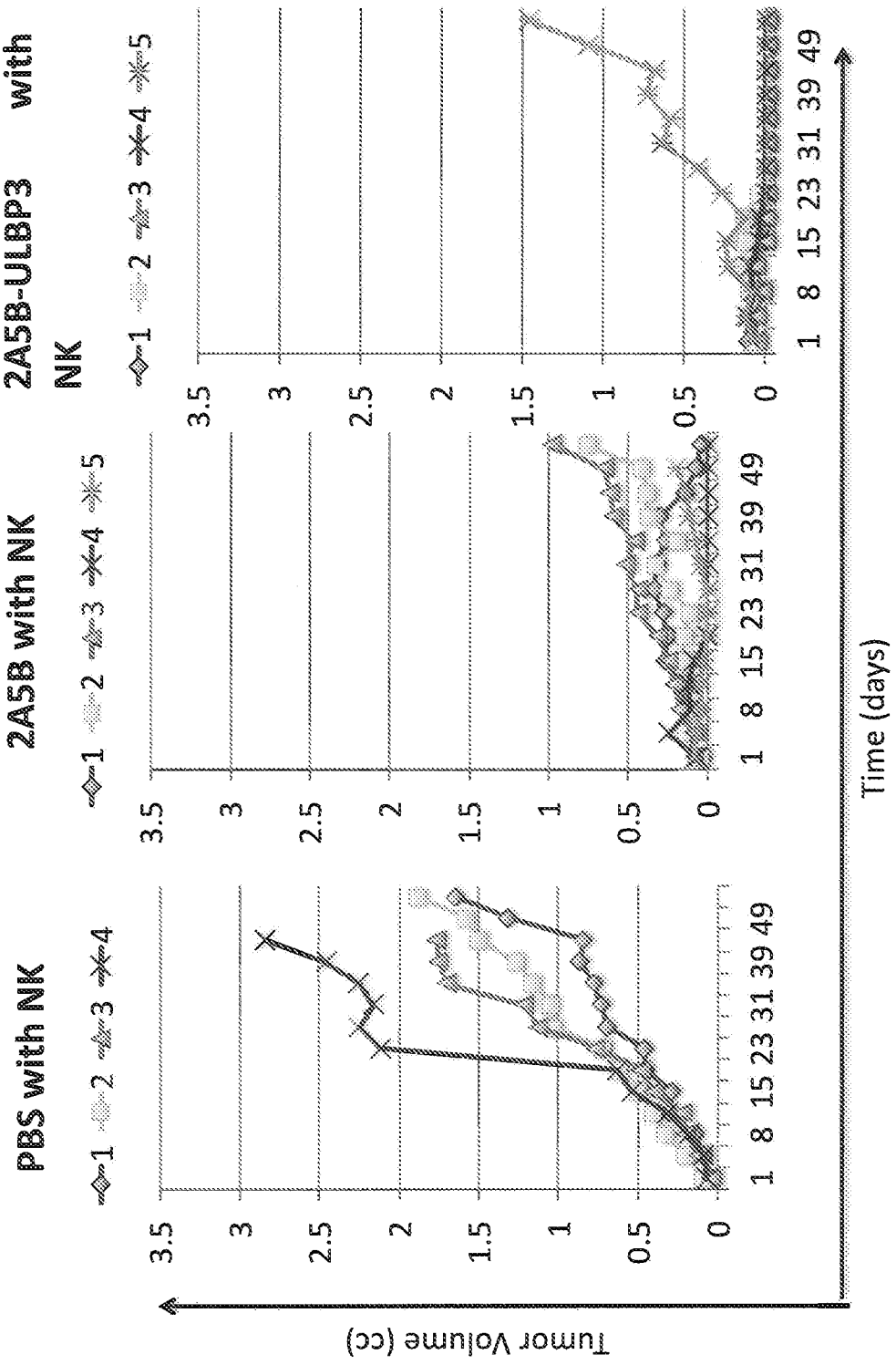

FIG. 22B presents data comparing the tumor suppressing ability of the oncolytic HSV vector, 2A5B ULBP3 (right panel), to the backbone vector (2A5B) (center panel) and also to sham (PBS)-treated animals (left column), each in the presence of NK cells.

DETAILED DESCRIPTION OF THE INVENTION

The present invention provides a recombinant viral vector with one or more exogenous genes (i.e., a gene not normally or natively found in the vector) that encodes for and causes expression of a NKG2D activating ligand in a host cell that is infected with the viral vector. The NKG2D activating ligand is expressed after infection of a cell with the viral vector. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. A viral vector may sometimes be referred to as a "recombinant virus" or a "virus." The terms "oncolytic virus" and "oncolytic vector" are used interchangeably herein. In some embodiments, the present invention provides for recombinant oncolytic viruses, which refer to a virus that has been modified to, or naturally, preferentially infect cancer cells. Examples of oncolytic viruses are known in the art including, but not limited to, herpes simplex virus, adenovirus, polio virus, vaccinia virus, measles virus, vesicular stomatitis virus, orthomyxovirus, parvovirus, maraba virus, or coxsackievirus Both replication competent and replication incompetent vectors can be used. The general methods described in International PCT Publication No. WO 2015/066042, which is incorporated in its entirety by reference, can be applied for engineering HSV vectors, including the knockout and/or regulation of HSV replication genes.

Replication incompetent vectors can be produced by deletions, mutations or other alterations (e.g., insertions) of one or more essential viral genes. As used herein, "essential viral genes" refer to viral genes that are required for viral replication. Genes required for replication of a variety of viruses are known in the art. In some embodiments of the present invention, the vector is an HSV vector and comprises one or more deletions, mutations or other alterations (e.g., insertions) in one or more of the ICP0, ICP4, ICP22, ICP27 and ICP47 loci. In some embodiments, the viral vectors comprise deletions, mutations or other alterations (e.g., insertions) in all of the ICP0, ICP4, ICP22, ICP27 and ICP47 loci. In certain embodiments, the HSV vectors described herein contain one or more a deletions of the internal repeat (joint) region, which comprises one copy each of the diploid genes ICP0, ICP34.5, LAT and ICP4 along with the promoter for the ICP47 gene. In some embodiments, instead of deleting the joint, the expression of genes in the joint region, particularly ICP0 and/or ICP47, can be silenced by deletion or other means of inactivation of these genes.

In some embodiments, the viral vectors of the present invention comprise one or more exogenous genes. The term "exogenous gene" refers to a gene not normally or natively found in the vector (e.g., a transgene). Generally, the exogenous gene is expressed by a cell after infection of the cell with the viral vector. In some embodiments, an exogenous gene encodes for an NKG2D ligand. In some embodiments, the NKG2D ligand is an NKG2D activating ligand such as UL-16 Binding Protein (ULBP), including ULBP1, ULBP2, ULBP3, ULBP4, ULBP5, or ULBP6. In some embodiments, the NKG2D activating ligand is an MHC class I-related Chain A (MicA) or an MHC class I-related Chain B (MicB) protein. Without wishing to be bound by theory, it is believed that, when introduced into a cancer cell, the vector causes expression of the NKG2D activating ligand, thereby facilitating effector cell-mediated death of the cancer cell.

In some embodiments, the viral vectors described herein comprise a first exogenous gene encoding an NKG2D ligand and a second exogenous gene encoding an oncolytic factor. As used herein, the term "oncolytic factor" refers to any protein or nucleic acid that enhances the tumor-lysing capabilities of the vectors described herein. While an NKG2D ligand alone can recruit/activate effector cells to lyse tumor cells, expression of an additional oncolytic factor may increase the therapeutic efficacy of the vectors described herein. Exemplary oncolytic factors include proteases such as metalloproteinases (for example, as a non-limiting example, matrix metalloproteinase (MMP)-9 (MMP9), a prodrug-converting enzyme, cytosine deaminase, thymidine kinase, or purine nucleoside phosphorylase. Table 1 presents suitable extracellular matrix (ECM) enzymes (MMPs, ADAMTSs, and hyaluronidases) and their respective targets, which are suitable for inclusion into the inventive vector as oncolytic factors.

The vector can also cause expression of an oncolytic factor by the host cell. When formulated into a pharmaceutical composition and administered to a patient, the vector can be used to treat cancer. The cancer can be a glioblastoma including one with an isocitrate dehydrogenase (IDH) mutation (IDH$^{Mut}$). An exemplary glioblastoma is glioblastoma multiforme (GBM).

For the purposes of this disclosure, a Herpes Simplex Virus (HSV) vector is exemplified together with use in treating glioblastoma including IDH$^{Mut}$ glioblastoma. Nonetheless, other cellular targets and other viral vectors are contemplated for expressing NKG2D ligands including adenoviral, retroviral, and adeno-associated viral vectors, as are well known in the art. Such vectors can be constructed using methods known to persons of ordinary skill in the art.

As discussed below, it has been found that ULBP1 and ULBP3 are significantly down-regulated (expressed in lower amounts) in IDH$^{Mut}$ (those with isocitrate dehydrogenase (IDH) mutations) relative to IDH wildtype (WT, IDH$^{WT}$) gliomas. Thus, expression of one or both of ULBP1 and ULBP3 in cancer cells via a viral vector can be advantageous. In various embodiments, some variation from the WT ULBP sequences can be acceptable (i.e., still yielding sensitization to NK cells). For example, the ULBP proteins can have 70, 75, 80, 85, 90, 91, 92, 93, 94, 95, 96, 97 98, 99, or 100% sequence identity with the mature ULBP protein of any of ULBP1, ULBP2, ULBP3, ULBP4, ULBP5, or ULBP6. Sequence identity can be determined, for example, by manual alignment or using the Needleman-Wunsch method. Nucleic acids encoding the vectors are also contemplated, including variations in sequence that retain function of the vector or due to degeneracy of the genetic code.

Because the vector may infect both cancer cells and noncancerous cells, in some embodiments, the expression of the one or more exogenous genes (e.g., an NKG2D activating ligand and/or ECM protease) is controlled by a cellular biomolecule (e.g., small molecule, macromolecule, or complex). In certain embodiments, the cellular biomolecule regulates the expression of the one or more exogenous genes comprised within the viral vector, such as an NKG2D ligand or an ECM protease. As used herein, a cellular biomolecule is a molecule that is endogenously expressed by a cell that is capable of binding to one or more nucleic acid sequences comprised within the vector, thereby regulating the expression of one or more genes encoded by the vector. The cellular biomolecule may a small molecule (e.g., a hormone), a protein, a nucleic acid, or macromolecule. In certain embodiments, the cellular biomolecule regulates the expression of the one or more exogenous genes comprised within the viral vector, such as an NKG2D ligand or an ECM protease. In some embodiments, the cellular biomolecule is a microRNA (miRNA or miR), such as miR122, miR124, miR128, miR137, and/or miR199.

The cellular biomolecule may negatively regulate (e.g., the expression of the cellular biomolecule decreases expression of one or more genes) the expression of one or more genes encoded by the vector. For example, in some embodiments, expression of the one or more genes comprised in the viral vector (e.g., exogenous genes and/or essential genes) is controlled by a cellular biomolecule that is present at a greater concentration in noncancerous cells compared to cancerous cells. In such embodiments, the increased expression of the cellular biomolecule in the non-cancerous cell can decrease expression of the exogenous genes and/or essential genes in the non-cancerous cell, while allowing for expression of the exogenous genes and/or essential genes in the cancerous cells. In such embodiments, the differential expression of the cellular biomolecule results in reduced cytotoxicity (e.g., NK-cell mediated cytotoxicity) toward non-cancerous cells.

The cellular biomolecule can be one that occurs in greater concentration in noncancerous cells than in the cancer cell. By placing the gene under negative control of the biomolecule, the NKG2D activating ligand will be preferentially expressed in a cancer cell relative to noncancerous cells that might become infected by the vector. Without wishing to be bound by theory, this may reduce cytotoxicity to noncancerous cells and thereby increase safety or allow an increase in dose for added efficacy (i.e., to increase the therapeutic window). Relative NK recruitment can be measured according to assays as illustrated using the figures herein and as otherwise known to those of ordinary skill in the art. The biomolecule can act via a promoter in operable linkage to the NKG2D activating ligand gene, a regulatory element controlling translation of an NKG2D activating ligand-interfering RNA, an element that induces degradation of NKG2D activating ligand mRNA, or other regulatory scheme known in the art. Alternately, or in addition, a corresponding positive control scheme can be used for cellular biomolecules that occur in greater concentration in cancer cells relative to noncancerous cells. Relative NK recruitment can be measured according to assays as illustrated using the figures herein and as otherwise known to those of ordinary skill in the art.

In some embodiments, the cellular biomolecule positively regulates (e.g., the presence of the cellular biomolecule increases expression of one or more genes) the expression of one or more genes. For example, in some embodiments, expression of the one or more genes comprised in the viral vector (e.g., exogenous genes and/or essential genes) is controlled by a cellular biomolecule that is present at a greater concentration in cancerous cells compared to non-cancerous cells. In such embodiments, the increased expression of the cellular biomolecule in the cancerous cell may increase expression of the exogenous genes and/or essential genes in the cancerous cell, while preventing expression of the exogenous genes and/or essential genes in the non-cancerous cells. In such embodiments, the differential expression of the cellular biomolecule results in reduced cytotoxicity (e.g., NK-cell mediated cytotoxicity) toward non-cancerous cells. The biomolecule can act via a promoter in operable linkage to the NKG2D activating ligand gene, a regulatory element controlling translation of an NKG2D activating ligand-interfering RNA, an element that induces degradation of NKG2D activating ligand mRNA, or other regulatory scheme known in the art.

In some embodiments, the cellular biomolecule is a micro-RNA (miRNA or miR), and an miRNA control polynucleotide is included in the vector. An miRNA control polynucleotide comprises one or more miRNA target sequences or response elements (RE) comprising the reverse complement of the miRNA. In some embodiments, the miRNA can be mir122, mir124, mir128, mir137, or mir199. Multiple control polynucleotides (e.g., miRNA target sequences) can be included in one or more genes comprised within the viral vectors can also be used to recognize more than one miRNA. For example, as exemplified below, the miRNA can be mir124 and the cancer cell can be a glioblastoma cell. mir124 is known to be expressed in much greater amounts in normal (e.g., non-cancerous) cells than in at least some glioblastoma cells (i.e., 10% greater, 20% greater, 30% greater, 40% greater, 50% greater, 60% greater, 70% greater, 80% greater, 90% greater, 95% greater, 99% greater or 100% greater compared to non-cancerous cells).

In some embodiments, the miRNA control polynucleotide can comprise one or more miRNA target sequences. For example, the miRNA control polynucleotide can comprise 1, 2, 4, 5, 6, or more miRNA target sequences. In some embodiments, the sequences can be inserted in tandem and can be spaced apart by spacers of four or more nucleotides. Such response elements and method of use are disclosed in international PCT Publication No. WO 2015/066042, which is incorporated by reference herein.

TABLE 1

Exemplary ECM enzymes

| ECM Enzyme | ECM targets | Other targets |
|---|---|---|
| MMP1* | Collagens I, II, III, VII, and X; gelatins; aggrecan; entactin; tenascin; perlecan | IGFBP-2, -3, -5; pro-IL-1b; CTGF; MMP-2, -9 |
| MMP2*** | Gelatins; collagens IV, V, VII, X, and XI; fibronectin; laminin; elastin; aggrecan | Pro-TGF-b; FGF receptor I; MCP-3; IGFBP-5; pro-IL-1b; galectin-3; plasminogen |
| MMP-3* | Aggrecan; decorin; gelatins; fibronectin; laminin; collagens III, IV, IX, and X; tenascin; perlecan | IGFBP-3; pro-IL-1b; HB-EGF; pro-TGF-b; CTGF; E-cadherin; plasminogen; uPA; pro-MMP-1, -7, -8, -9, -1 |
| MMP-7 ** | Aggrecan; gelatins; fibronectin; laminin; elastin; entactin; collagen IV; tenascin; decorin | b4 integrin; E-cadherin; pro-TNFa; CTGF; HB-EGF; RANKL; IGFBP-3; plasminogen, MMP-1, -2, -9 |
| MMP-8* | Collagens I, II, and III; gelatins; aggrecan; | |
| MMP9*** | Gelatins; collagens III, IV, and V; aggrecan; elastin; entactin; vitronectin; N-telopeptide of collagen I | Pro-TGF-b; IL-2 receptor a; Kit-L; IGFBP-3; pro-IL-1b; ICAM-1; galectin-3; plasminogen |
| MMP-10* | Aggrecan; fibronectin; laminin; collagens III, IV, and V | Pro-MMP-1, -8, -10 |
| MMP-11* | Fibronectin; laminin; aggrecan; gelatins | IGFBP-1 |
| MMP-12* | Elastin; aggrecan; fibronectin; osteonectin; laminin; nidogen | Plasminogen |
| MMP-13* | Collagens I, II, III, IV, IX, X, and XIV; aggrecan; fibronectin; tenascin; SPARC/osteonectin; laminin; perlecan | CTGF; pro-TGF-b; MCP-3 |
| MMP14**** | Collagens I, II, and III; gelatins; aggrecan; fibronectin; laminin; fibrin; | pro-MMP-2; pro-MMP-13; CD44; MCP-3; tissue transglutaminase |
| MMP15**** | Fibronectin; laminin; tenascin; nidogen; aggrecan; perlecan | Pro-MMP-2; tissue transglutaminase |
| MMP16**** | Collagen III; fibronectin; gelatin | Pro-MMP-2; tissue transglutaminase |
| MMP17**** | Gelatin; fibrinogen | |
| MMP-21* | Unknown | |
| MMP24**** | Fibrin, gelatin | Pro-MMP-2 |
| MMP25**** | Gelatin; collagen IV; fibrin; fibronectin; laminin | Pro-MMP-2 |

TABLE 1-continued

Exemplary ECM enzymes

| ECM Enzyme | ECM targets | Other targets |
|---|---|---|
| MMP-26** | Gelatin; collagen IV; fibronectin; fibrinogen; vitronectin | Pro-MMP-9 |
| MMP-27* | Unknown | |
| ADAMTS-1 | Aggrecan, versican | |
| ADAMTS-2 | Processing of procollagens I, II, and III N-propeptides | |
| ADAMTS-3 | Processing of procollagen II N-propeptides | |
| ADAMTS-4 | Aggrecan, brevican, versican, fibronectin, decorin | |
| ADAMTS-5 | Aggrecan, versican, brevican | |
| ADAMTS-6 | Unknown | |
| ADAMTS-7 | Cartilage oligomeric protein | |
| ADAMTS-8 | Aggrecan | |
| ADAMTS-9 | Aggrecan | |
| ADAMTS-10 | Unknown | |
| ADAMTS-12 | Unknown | |
| ADAMTS-13 | von Willebrand factor | |
| ADAMTS-14 | Processing of procollagen I N-propeptides | |
| ADAMTS-15 | Aggrecan | |
| ADAMTS-16 | Aggrecan | |
| ADAMTS-17 | Unknown | |
| ADAMTS-18 | Aggrecan | |
| ADAMTS-19 | Unknown | |
| ADAMTS-20 | Aggrecan | |
| HYAL1 | Unknown | |
| HYAL2 | high-molecular weight HA (CD44 ligand) | |
| HYAL3 | Unknown | |
| HYAL4 | Unknown | |
| HYAL5 | Unknown | |

*Basic domains (prodomain ▷ catalytic domain ▷ hemopexin-containing ancillary domain)
**Minimal domains (prodomain ▷ catalytic domain)
***MMPs with fibronectin-domain inserts
****Membrane-bound MMP anchored by GPI or a transmembrane domain (TM)

PCT Publication No. WO 2015/066042 discloses oncolytic HSV (oHSV) in which a replication gene is placed under control of mir124 so that it will selectively kill glioblastoma cells, and such a strategy can be employed in the context of the present invention as well. Vector tropism also can be modified by expressing surface-cell binding protein, for example as disclosed in PCT Publication No. WO 2015/066042.

A polynucleotide encoding the NKG2D activating ligand can be part of an exogenous expression cassette. In some embodiments of the vectors described herein, the encoding sequences within the exogenous expression cassette(s) can be in operable linkage with any desired genetic regulatory sequence, such as constitutive promoters or inducible or tissue-specific promoters, many examples of which are known in the art. For example, a commonly-employed constitutive promoter is the human cytomegalovirus (hCMV) promoter, and other promoters also can be used, e.g., the CMV early enhancer/chicken beta actin (CAG) promoter, and HSV immediate early promoter (e.g., ICP4 promoter), and the like.

A preferred vector according to the present invention is an HSV vector comprising transgenes encoding MMP9, one or both or ULPB1 and/or ULPB3, and optionally an antibody against PD-L1. As depicted in FIGS. 12A and 12B, the ULPB1, ULPB3 (or other ULPB) is preferably under expression control of a miRNA sequence, such as miR124. Sequences of ULPB1 (SEQ ID NO:1) and ULPB3 (SEQ ID NO:2), respectively, including miR124 control elements are set forth as follows:

TABLE 2

Exemplary ULBP Nucleic Acid Sequences

| ULBP | Nucleic acid sequence | SEQ ID NO: |
|---|---|---|
| ULBP1 | ATGTCTGCACTTCTGATCCTAGCTCTTGTTGGAGCTGCAGTTGCTGACTACAAAGACC ATGACGGTGATTATAAAGATCATGACATCGATTACAAGGATGACGATGACAAGCTTGG CTGGTCCCGGGCAGGATGGGTCGACACACACTGTCTTTGCTATGACTTCATCATCACT CCTAAGTCCAGACCTGAACCACAGTGGTGTGAAGTTCAAGGCCTGGTGGATGAAAGGC CTTTTCTTCACTATGACTGTGTTAACCACAAGGCCAAAGCCTTTGCTTCTCTGGGGAA GAAAGTCAATGTCACAAAAACCTGGGAAGAACAAACTGAAACACTAAGAGACGTGGTG GATTTCCTTAAAGGGCAACTGCTTGACATTCAAGTGGAGAATTTAATACCCATTGAGC CCCTCACCCTGCAGGCCAGGATGTCTTGTGAGCATGAAGCCCATGGACACGGCAGAGG ATCTTGGCAGTTCCTCTTCAATGGACAGAAGTTCCTCCTCTTTGACTCAAACAACAGA AAGTGGACAGCACTTCATCCTGGAGCCAAGAAGATGACAGAGAAGTGGGAAGAACA GGGATGTGACCATGTTCTTCCAGAAGATTTCACTGGGGGATTGTAAGATGTGGCTTGA AGAATTTTTGATGTACTGGGAACAAATGCTGGATCCAACAAAACCACCCTCTCTGGCC CCAGGCACAACCCAACCCAAGGCCATGGCCACCACCCTCAGTCCCTGGAGCCTTCTCA TCATCTTCCTCTGCTTCATTCTAGCTGGCAGATGAGAATTCGGCATTCACCGCGTGCC TTATAGTACCAGGGCATTCACCGCGTGCCTTAAGGATCCTGGCATTCACCGCGTGCCT TAATGACTGCGGCATTCACCGCGTGCCTTAagatcT | 1 |
| ULBP3 | ATGTCTGCACTTCTGATCCTAGCTCTTGTTGGAGCTGCAGTTGCTGACTACAAAGACC ATGACGGTGATTATAAAGATCATGACATCGATTACAAGGATGACGATGACAAGCTTTT CGACTGGTCCGGGACGGGGCGGGCCGACgCTCACTCTCTCTGGTATAACTTCACCATC ATTCATTTGCCCAGACATGGGCAACAGTGGTGTGAGGTCCAGAGCCAGGTGGATCAGA AGAATTTTCTCTCCTATGACTGTGGCAGTGACAAGGTCTTATCTATGGGTCACCTAGA | 2 |

TABLE 2-continued

Exemplary ULBP Nucleic Acid Sequences

| ULBP | Nucleic acid sequence | SEQ ID NO: |
|---|---|---|
| | AGAGCAGCTGTATGCCACAGATGCCTGGGGAAAACAACTGGAAATGCTGAGAGAGGTG<br>GGGCAGAGGCTCAGACTGGAACTGGCTGACACTGAGCTGGAGgATTTCACACCCAGTG<br>GACCCCTCACGCTGCAGGTCAGGATGTCTTGTGAGTGTGAAGCCGATGGATACATCCG<br>TGGATCTTGGCAGTTCAGCTTCGATGGACGGAAGTTCCTCCTCTTTGACTCAAACAAC<br>AGAAAGTGGACAGTGGTTCACGCTGGAGCCAGGCGGATGAAAGAGAAGTGGGAGAAGG<br>ATAGCGGACTGACCACCTTCTTCAAGATGGTCTCAATGAGAGACTGCAAGAGCTGGCT<br>TAGGGACTTCCTGATGCACAGGAAGAAGAGGCTGGAACCCACAGCACCACCCACCATG<br>GCCCCAGGCTTAGCTCAACCCAAAGCCATAGCCACCACCCTCAGTCCCTGGAGCTTCC<br>TCATCATCCTCTGCTTCATCCTCCCTGGCATCTGAGAATTCGGCATTCACCGCGTGCC<br>TTATAGTACCAGGGCATTCACCGCGTGCCTTAAGGATCCTGGCATTCACCGCGTGCCT<br>TAATGACTGCGGCATTCACCGCGTGCCTTA | |

The inventive vector can be produced by standard methods known to persons of ordinary skill in the field of virology. However, to facilitate manipulation of the genome and production of the vectors described herein, the invention also provides a nucleic acid encoding the inventive vector. Optionally, the nucleic acid is a bacterial artificial chromosome (BAC) encoding the inventive vector, which facilitates manipulation of the vector, particularly when it is an HSV, in a bacterial system.

It should be recognized that the vectors described herein can be used to target and kill cancerous cells, whether in vivo or in vitro. In some embodiments, the vectors described herein are employed therapeutically in the treatment of human patients against human tumor cells to treat cancer. However, the method can also be employed in other mammals, such as companion animals (e.g., cats and dogs), or animals of agricultural importance (e.g., cattle, sheep, horses, and the like), or of zoological or laboratory (e.g., rats, mice, etc.) importance. In some embodiments, the invention relates to a method of treating cancer in a subject in need thereof, comprising administering a prophylactically effective amount or a therapeutically effective amount of an oncolytic virus, a viral stock, or a composition as described herein to the subject. A "subject," as used herein, includes any animal that exhibits a symptom of a disease, disorder, or condition that can be treated with the recombinant viral vectors, compositions, and methods disclosed herein. Suitable subjects (e.g., patients) include laboratory animals (such as mouse, rat, rabbit, or guinea pig), farm animals (such as horse or cow), and domestic animals or pets (such as cat or dog). Non-human primates and, preferably, human patients, are included. A suitable subject can be selected. For example, a human patient suffering from a IDH$^{Mut}$ glioblastoma can be diagnosed and selected for administration (e.g., intracranial and intratumoral) of a pharmaceutical composition comprising a vector with an expression cassette that produces the NKG2D activating ligand, optionally under control of an mir124 response element. Accordingly, an NK and/or T-cell based immune response can be mounted against the glioblastoma by the subject's immune system Generally, the vectors described herein are most useful when enough of the virus (vector) can be delivered to a cell population to ensure that the cells are confronted with a suitable number of viruses (vector particles). Thus, the present invention provides a stock, preferably a homogeneous stock, comprising the vectors described herein. The preparation and analysis of viral stocks is well known in the art. For example, a viral stock can be manufactured in roller bottles containing cells transduced with the vector. The viral stock can then be purified on a continuous nycodenze gradient, and aliquotted and stored until needed. Viral stocks vary considerably in titer, depending largely on viral genotype and the protocol and cell lines used to prepare them. Preferably, such a stock has a viral titer of at least about $10^5$ plaque-forming units (pfu)/mL, such as at least about $10^6$ pfu/mL or even more preferably at least about $10^7$ pfu/mL, $10^8$ pfu/mL, $10^9$ pfu/mL, $10^{10}$ pfu/mL, or $10^{11}$ pfu/mL. Such titers can be established using cells that express a receptor to which the vector is targeted, for example.

The invention additionally provides a composition comprising the inventive vector and a carrier, preferably a physiologically-acceptable carrier. The carrier of the composition can be any carrier suitable for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there exists a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

The compositions and vectors described herein can be delivered to a subject in need thereof at an appropriate dose or a therapeutically effective amount. As used herein, "appropriate dose" and "therapeutically effective amount" refer to the amount of a composition or recombinant vector described herein required to achieve a desired physiologic and/or biological outcome. A "therapeutically effective amount" of a virus, a viral stock, or a composition may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). One of skill in the art will understand that the therapeutically effective amount will vary based on the type of virus being administered, nature of the formulation, route of administration, nature and/or severity of the disease to be treated, and/or general health and well-being of the subject. In some embodiments, the appropriate dose is in the range of $10^2$ to $10^{11}$ pfu or $10^4$ to $10^{10}$ pfu. The term "treating" and "treatment" as used herein refers to administering to a subject a therapeutically effective amount of a recombinant virus or composition thereof as described herein so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease.

Some aspects of the invention encompass a method of killing a cancerous cell, comprising exposing the cancerous cell to an oncolytic virus described herein or compositions thereof under conditions sufficient for the oncolytic virus to infect and replicate within said cancerous cell, and wherein replication of the oncolytic virus within the cancerous cell results in cell death. A suitable subject can be selected. For example, a human patient suffering from a $IDH^{Mut}$ glioblastoma can be diagnosed and selected for administration (e.g., intracranial and intratumoral) of a pharmaceutical composition comprising a vector with an expression cassette that produces the NKG2D activating ligand, optionally under control of an mir124 response element. Accordingly, an NK and/or T-cell based immune response can be mounted against the glioblastoma by the subject's immune system.

"Administration" refers herein to introducing an oncolytic virus, a viral stock, or a composition thereof into a subject or contacting an oncolytic virus, a viral stock, or a composition thereof with a cell and/or tissue. Administration can occur by injection, irrigation, inhalation, consumption, electro-osmosis, hemodialysis, iontophoresis, and other methods known in the art. The route of administration will vary, naturally, with the location and nature of the disease being treated. In some embodiments, the pharmaceutical composition can be administered directly to the tumor (intratumoral delivery); e.g., by injection, catheter infusion, and the like. Alternately the composition can be delivered intravenously, intra-arterially, nasally, lymphatically, intraperitoneally, intracranially, intrathecally, or via local vascular perfusion. Thus, the administration can be local or systemic.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to up regulate the body's natural defenses against disease, particularly against the cancer or tumor against which the inventive vector is to be used. Antibiotics, i.e., microbicides and fungicides, can be present to reduce the risk of infection associated with gene transfer procedures and other disorders.

The following examples for the purpose of illustrating various embodiments of the invention and are not meant to limit the present invention in any fashion. The present examples, along with the methods described herein, are exemplary, and are not intended as limitations on the scope of the invention. Alterations, modifications, and other changes to the described embodiments which are encompassed within the spirit of the invention as defined by the scope of the claims are specifically contemplated.

Example 1

This example recites observations that have been made with respect to the inventive vectors (disclosed in FIGS. 12A and 12B).

IDHmut astrocytes and primary glioma lines show a reduction in the relative expression of NKG2DLs compared with IDHwt astrocytes.

Reduced NKG2D levels in IDHmut cells correlates with impaired NK-mediated cytotoxicity and suggests a role for NK cell resistance in IDH mutant tumors.

Overexpression of ULBP3 in IDHmut and IDHwt sensitizes these cells to NK cell-mediated cytotoxicity and appears to produce significant growth arrest.

Example 2

This example recites observations that have been made with respect to the inventive vectors concerning ULBP1 and ULBP3 depletion by miR124.

The miR124RE sequence was cloned into the 3'UTR region of ULBP1 and ULBP3, generating the plasmids named pENTRcagFlagULBP1 and pENTRcagFlagULBP3. 293T cells were seeded in six-well plate ($5\times10^5$/well). The following day cells were co-transfected with 300 ng of ULBP1 or ULBP3 plasmid (pENTRcagFlagULBP1 and pENTRcagFlagULBP3) and 100 pmol of miR124, using Lipo2000 reagent. At 24 h post-transfection, cells were collected, washed twice in cold PBS and lysed in RIPA1X buffer (100 µl per well) for 20 min on ice. Cell lysates were cleared by centrifugation and analyzed by SDS-Page and WB, using an antibody anti-Flag and anti-tubulin.

Figure 1A:
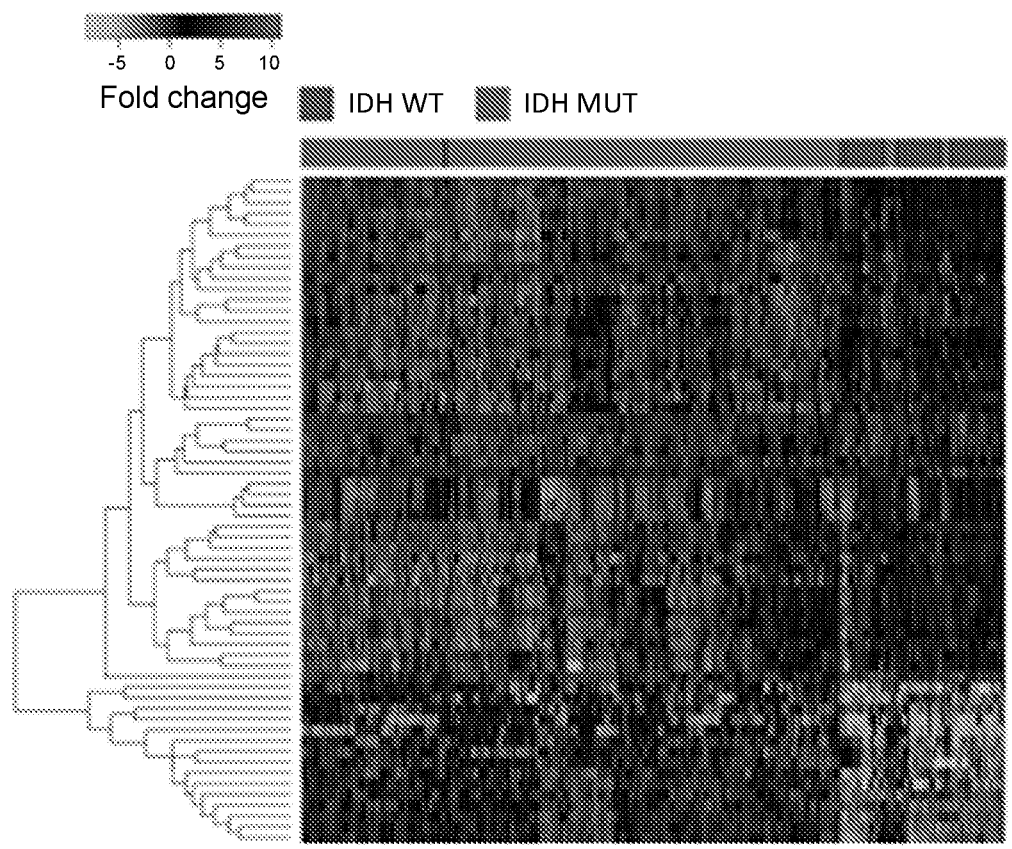
FIGS. 1A-1C demonstrate that NKG2D ligands are differentially expressed in IDH$^{Mut}$ gliomas. RNAseq analysis: 1639 immune-related genes (Gene Ontology Category 0050776) were compared in IDH$^{Mut}$ and IDH$^{WT}$ diffuse gliomas using the publically available RNAseq data from TCGA database from 286 individual diffuse glioma samples.
Figure 1B:
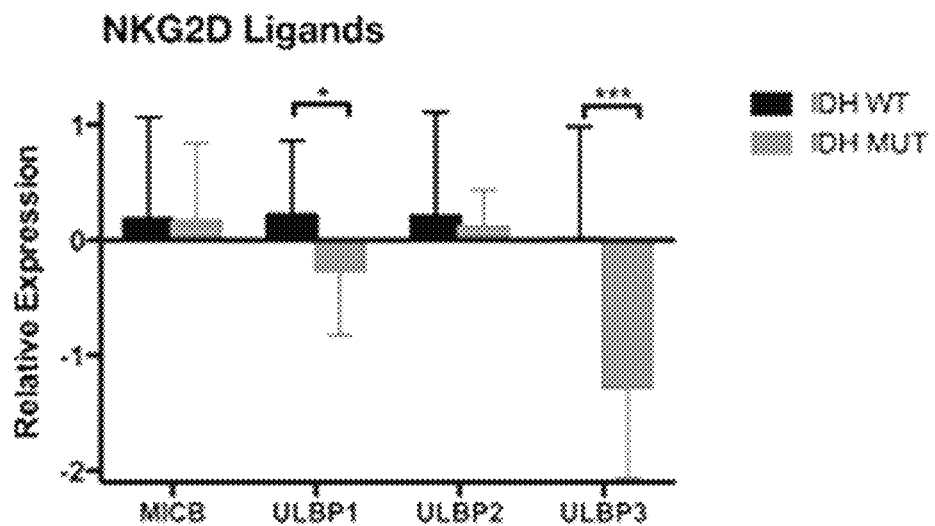
Figure 1C:
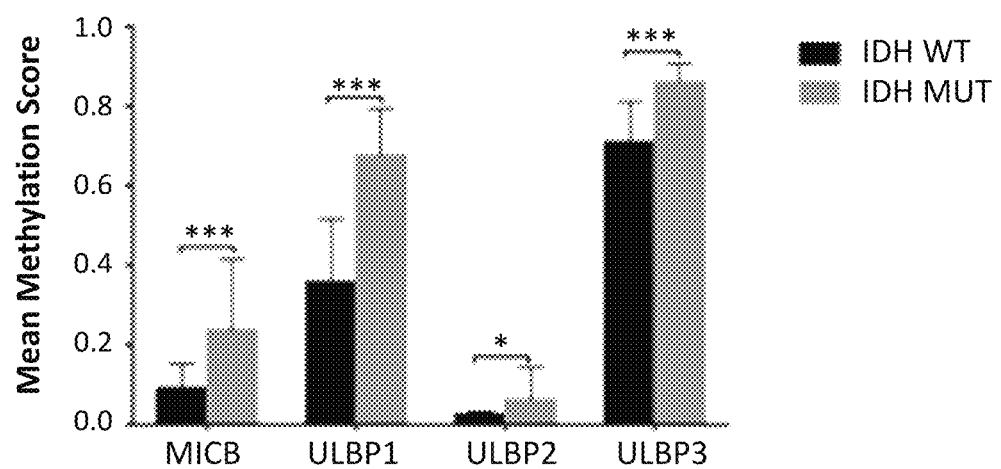
Figure 2A:
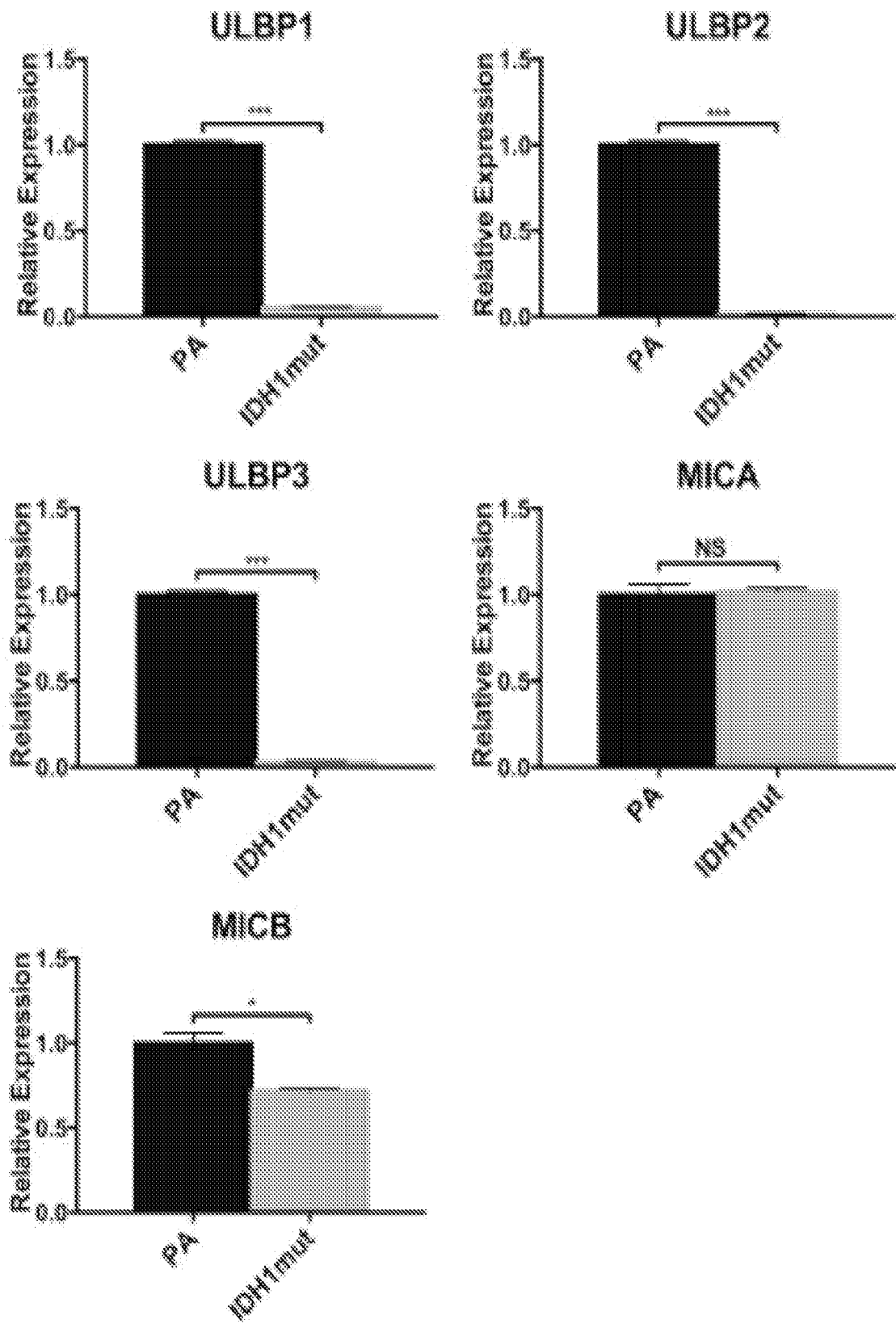
FIGS. 2A-2B demonstrate reduced expression of ULBP1, ULBP2, and ULBP3 in IDH$^{Mut}$ gliomas.
Figure 2B:
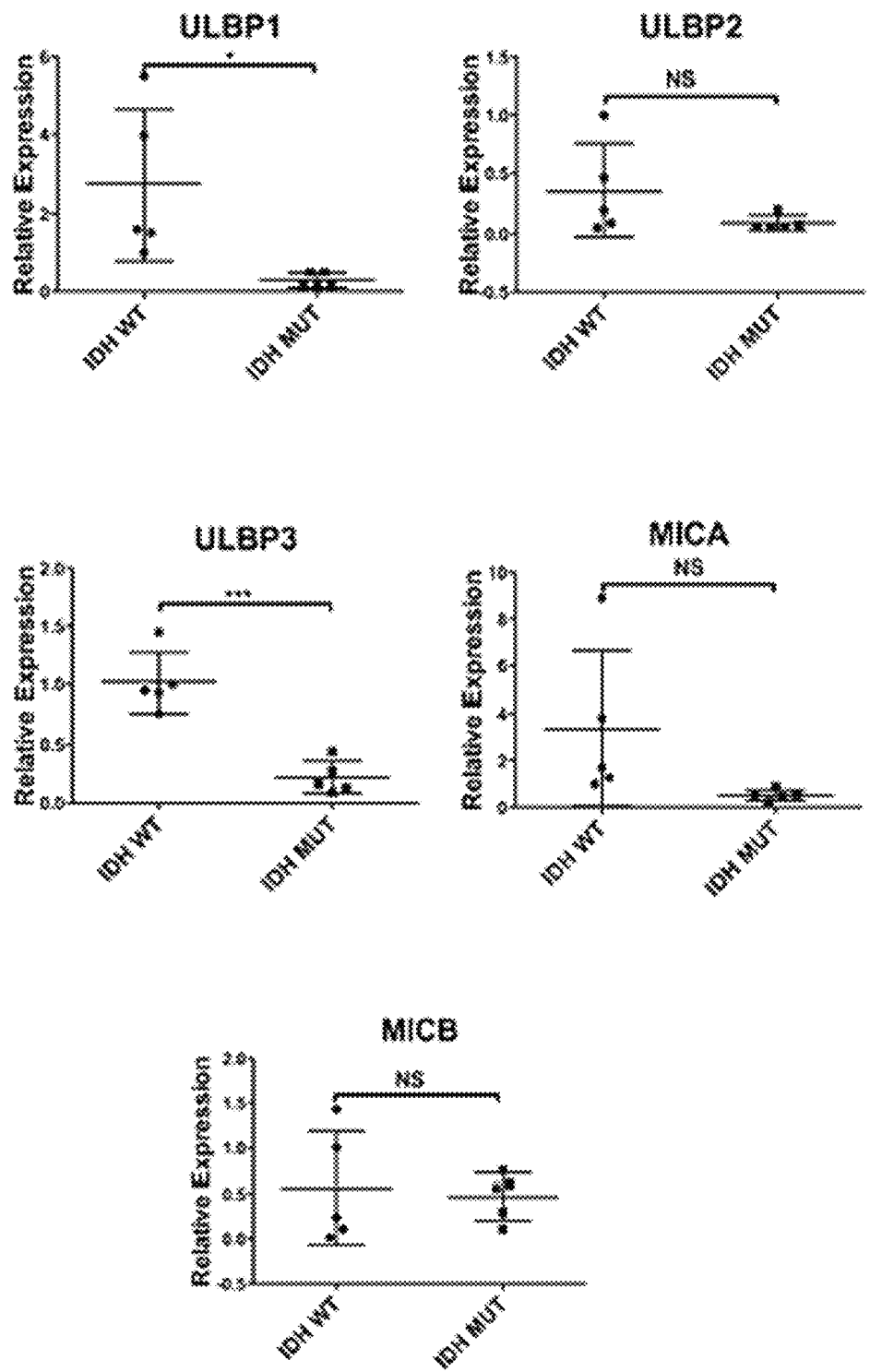
Figure 3A:
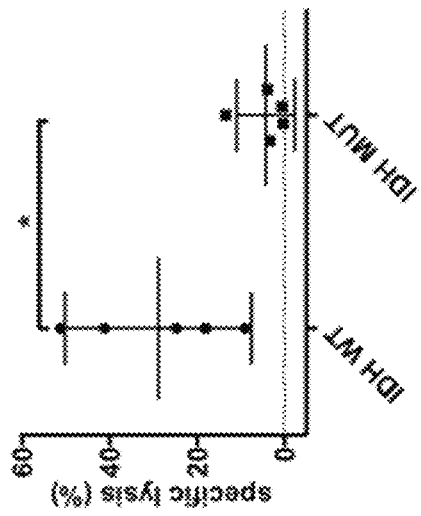
FIGS. 3A-3D demonstrate that IDH1$^{Mut}$ glioma cells are resistant to NK-mediated cytotoxicity. NK cell-mediated cytotoxicity was measured using a 7-AAD-based flow cytometry method in astrocytes or patient-derived GSCs. IFN-γ secretion in the supernatant was measured as a correlate for NK cell activation.
Figure 3B:
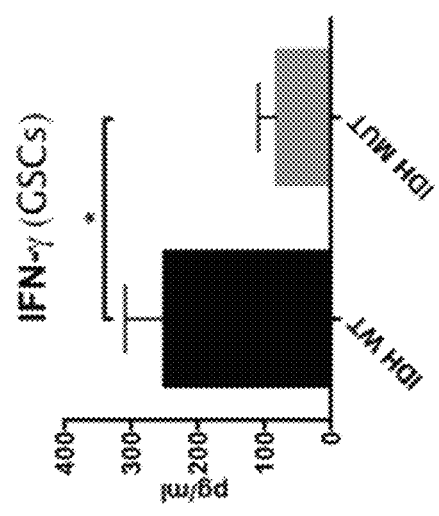
Figure 3C:
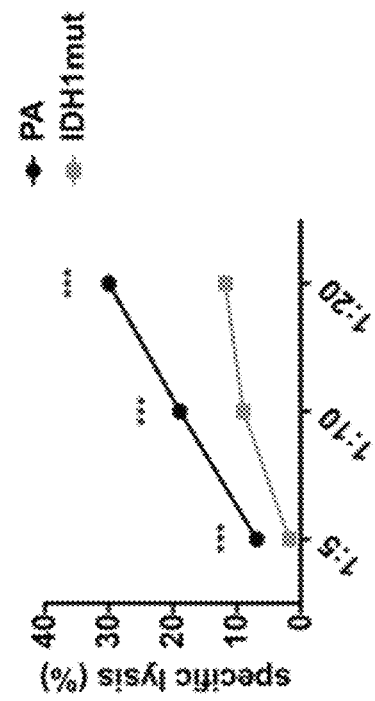
Figure 3D:
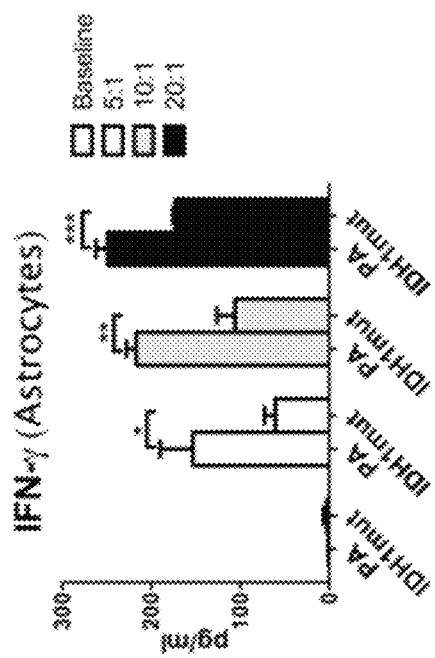
Figure 4A:
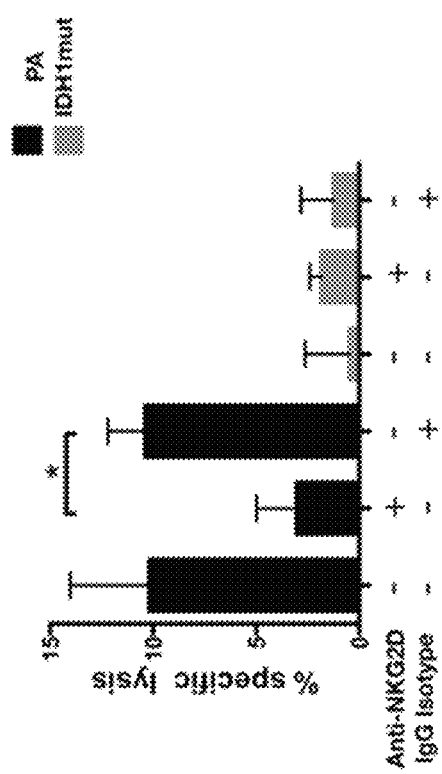
FIGS. 4A-4B demonstrate that NK-mediated killing in astrocytes is NKG2D-dependent.
Figure 4B:
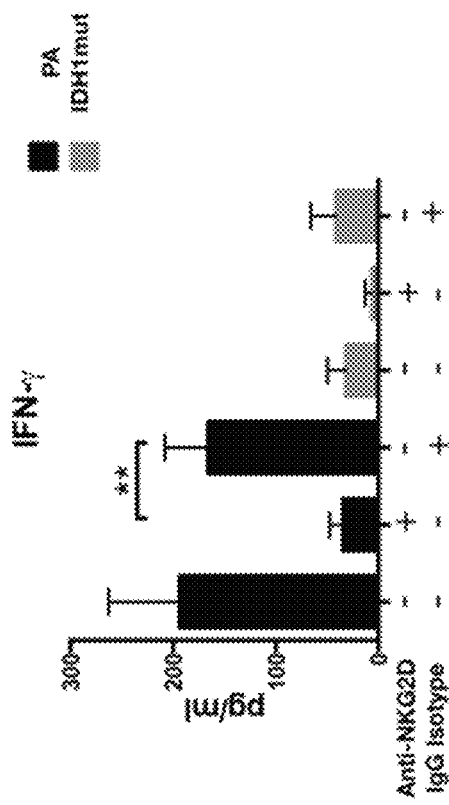
Figure 5:
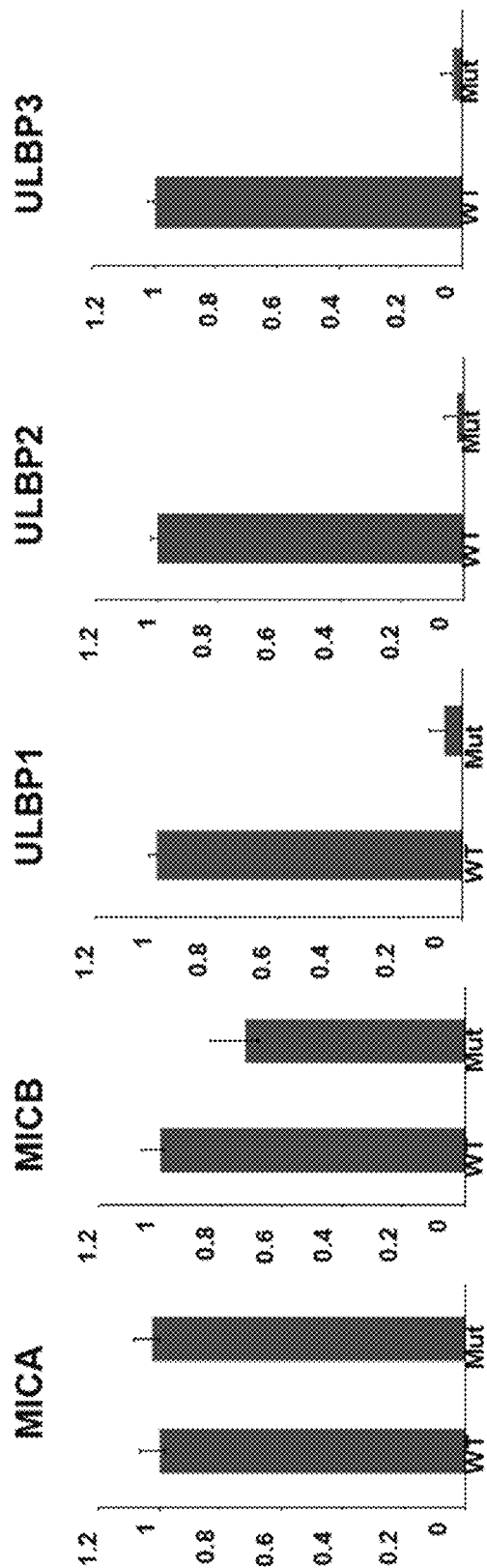
FIG. 5 shows expression of NKG2DLs in transduced primary human astrocytes. RT-qPCR analysis was performed on primary astrocytes stably transduced with either IDH$^{WT}$ (WT) or IDH$^{Mut}$ (Mut). ULBPs were significantly lower in IDH$^{Mut}$ compared to IDH$^{WT}$.
Figure 6:
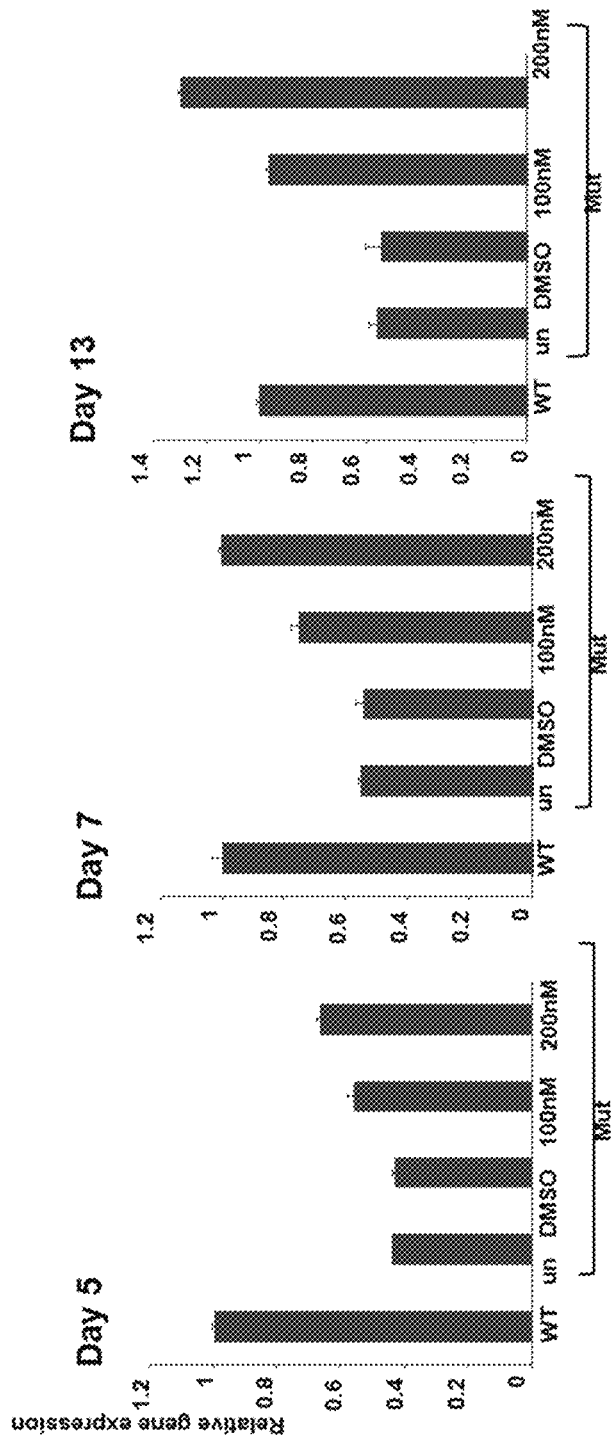
FIG. 6 demonstrates that decitabine (a DNA methyltransferase inhibitor) treatment restores ULBP3 expression. IDH$^{Mut}$ astrocytes (Mut) were treated with decitabine (100 nM or 200 nM), vehicle (DMSO) or left untreated (un) for 5, 7 or 13 days and ULBP3 expression was quantified by RT-qPCR. IDH$^{Mut}$ astrocytes treated for 7 days with decitabine (200 nM) showed ULBP3 expression of comparable to IDH$^{WT}$ (WT) astrocytes, suggesting that IDH mutation induces hypermethylation of the NK ligands.
Figure 7B:
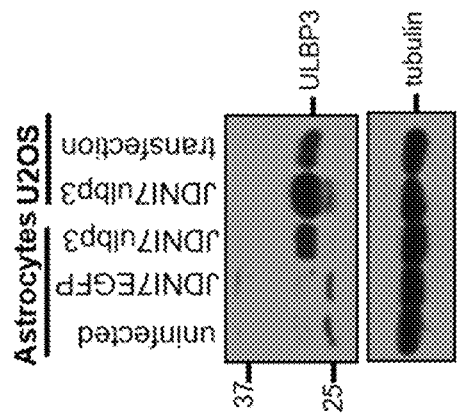
FIG. 7B demonstrates that astrocytes and U2OS cells infected with JΔNI7-FlagULBP3 express the tagged ULBP3 protein.
Figure 7A:
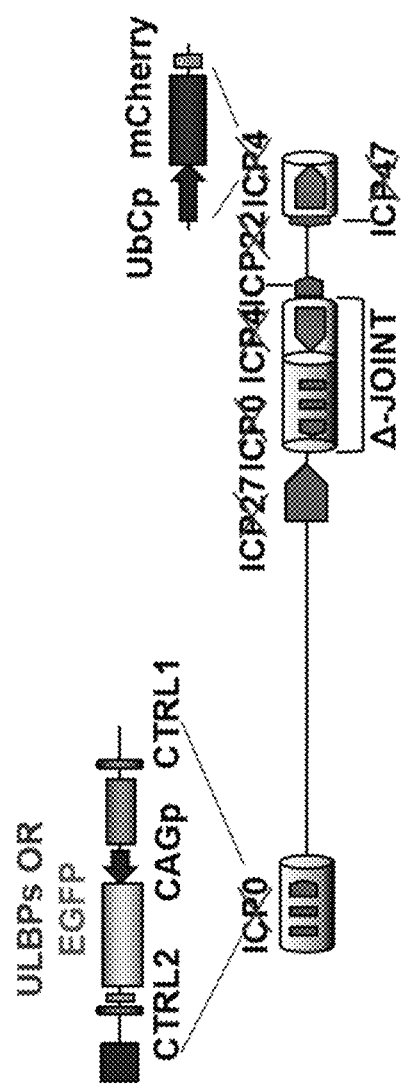
FIG. 7A shows a schematic representation of the HSV-defective vector JΔNI7. The ICP0, ICP4, ICP22, ICP27 and ICP47 genes are deleted or modified (black boxes) to block virus replication and expression of toxic immediate-early (IE) genes. Glycoprotein B (gB) is mutated for improved infection efficiency (Uchida et al., *J. Virol.* 84(23), 12200-09 (2010), incorporated herein in its entirety by reference). An mCherry expression cassette using the ubiquitin C promoter (UbCp) is inserted to monitor vector transcriptional activity. JΔNI7-GFP has a CAG promoter-driven EGFP cassette within the LAT locus while JΔNI7-ULBP3 has a CAG promoter-driven ULBP3 cassette.
Figure 8:
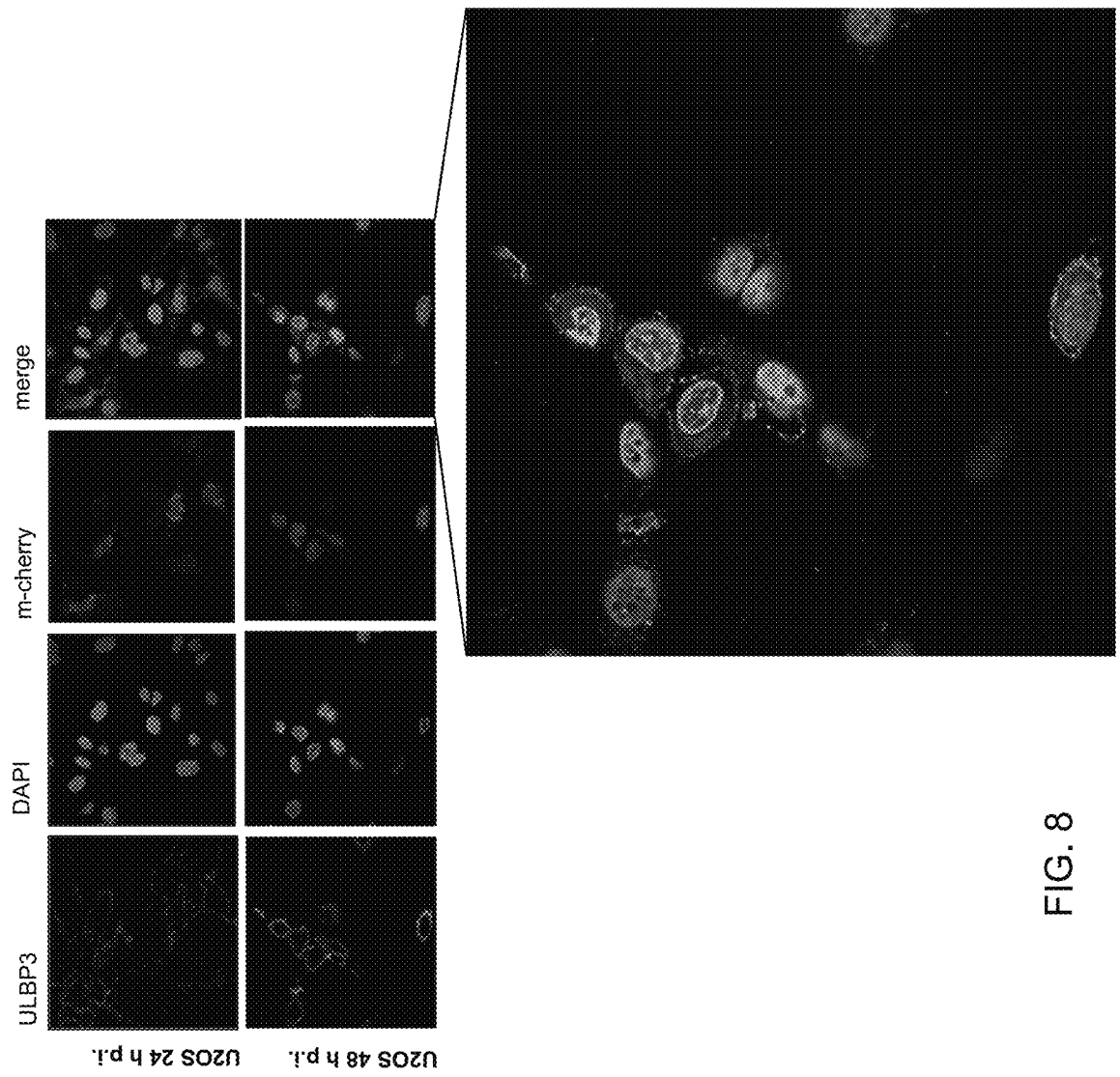
FIG. 8 demonstrates that U2OS cells infected with JΔNI7-FlagULBP3 express the tagged-protein that localizes as expected at the plasma membrane. U2OS cells were infected with JΔNI7-ULBP3 vector at an MOI of 5, time of imaging was 48 hours post-infection (h.p.i.).
Figure 9A:
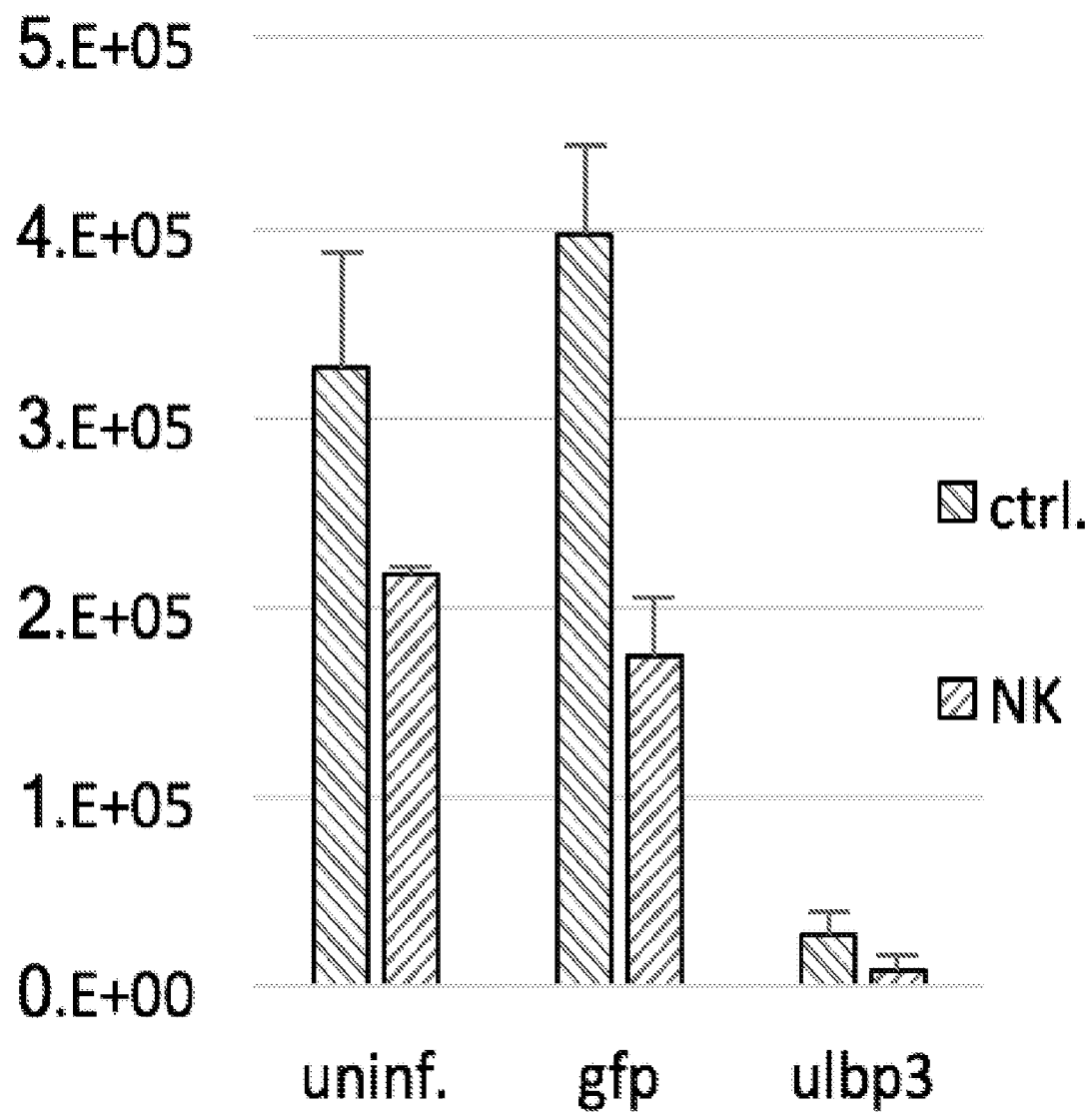
FIGS. 9A-9C demonstrate that ULBP3 expressed in $IDH^{Mut}$ cells by JΔNI7 induced NK cell activation and improved animal survival. $IDH^{WT}$ astrocytes (FIG. 9A) and $IDH^{Mut}$ astrocytes (FIG. 9B) were infected with either JΔNI7-EGFP (control vector) or JΔNI7-ULBP3 at an MOI of 10 for 5 days and overlayed with NK cells (10:1) for 48 hours. Cell-killing was measured by trypan blue.
Figure 9B:
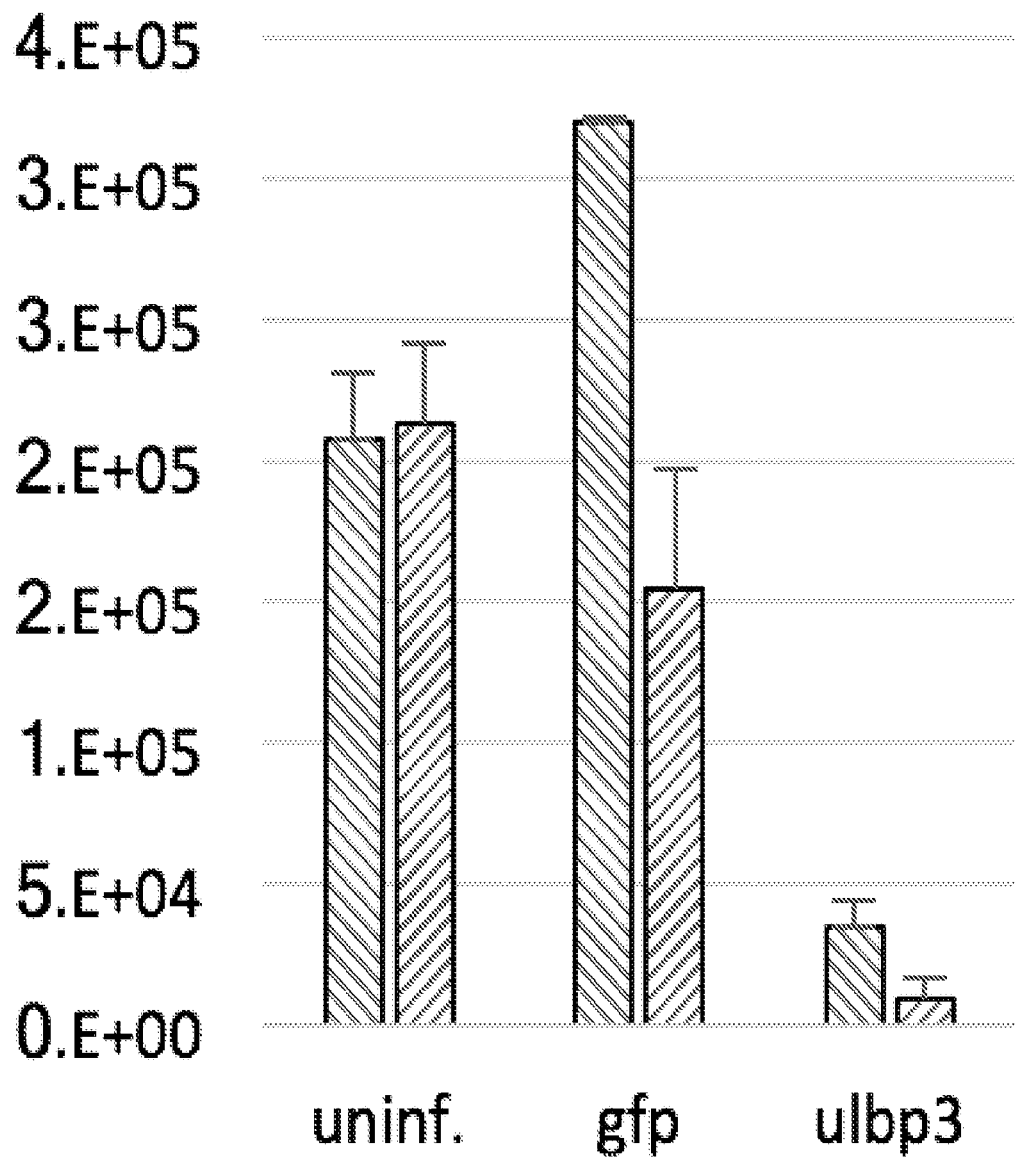
Figure 9C:
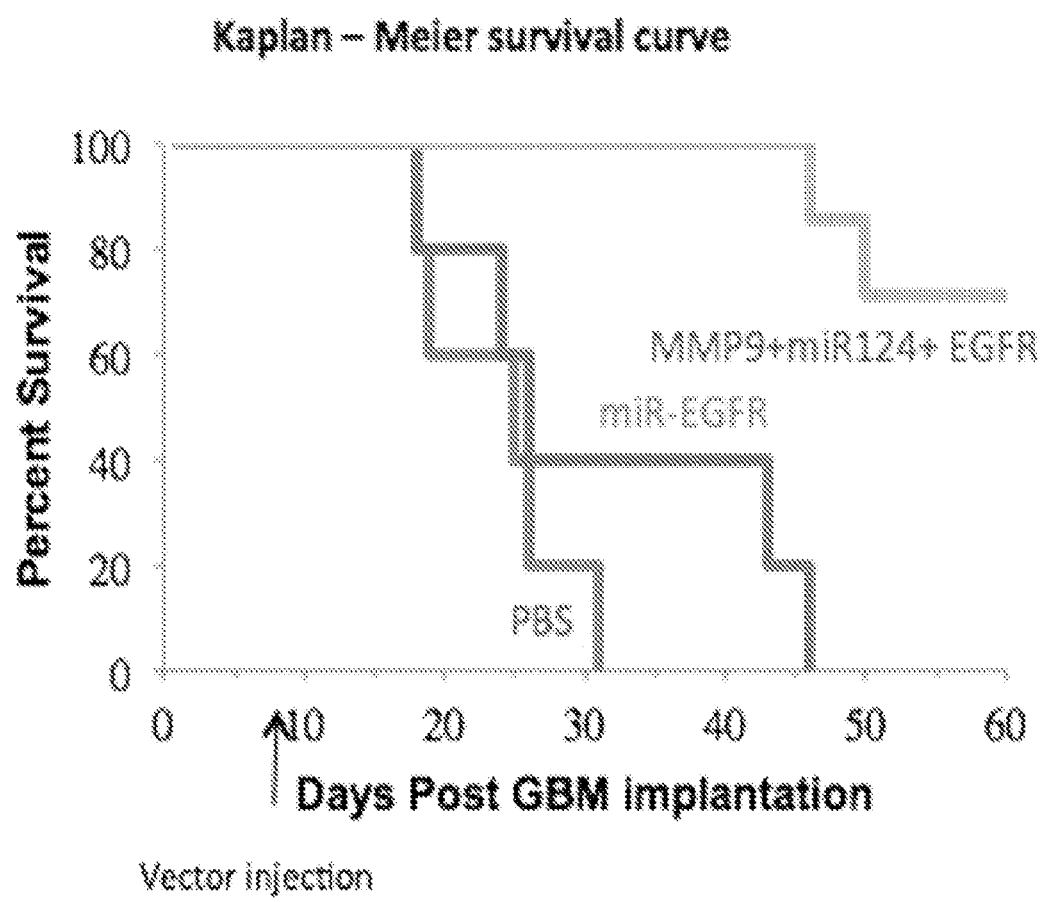
Figures 10A, 10B:
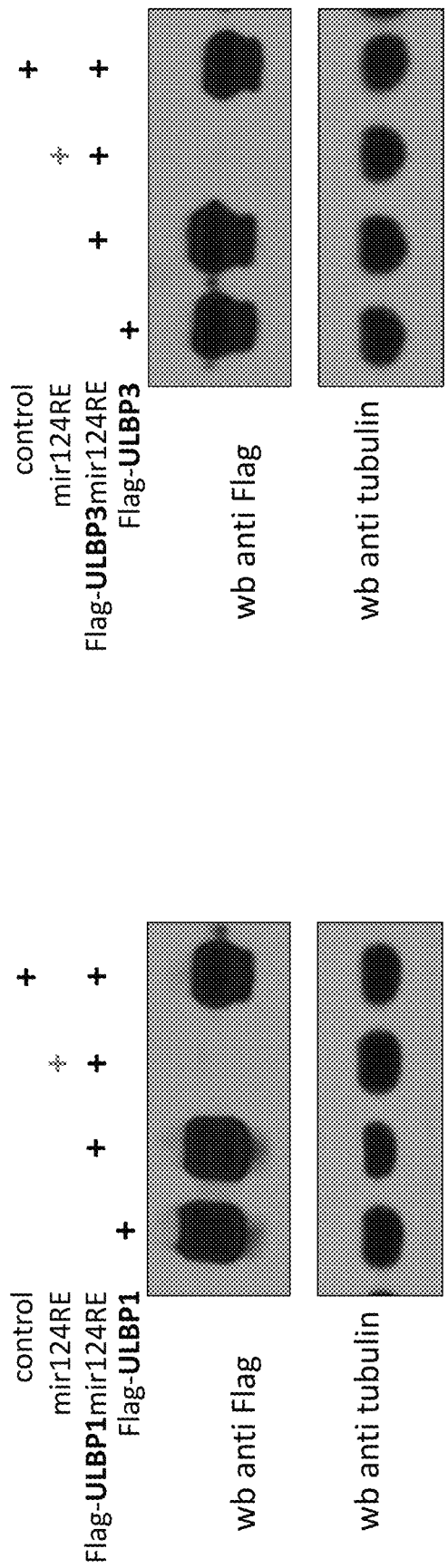
FIG. 10A and FIG. 10B show ULBP1 and ULBP3 depletion, respectively, by miR124. miR124 inhibits ULBP1 and ULBP3 expression, suggesting that this approach can be used to block the proteins' expression in normal neurons.
Figure 11:
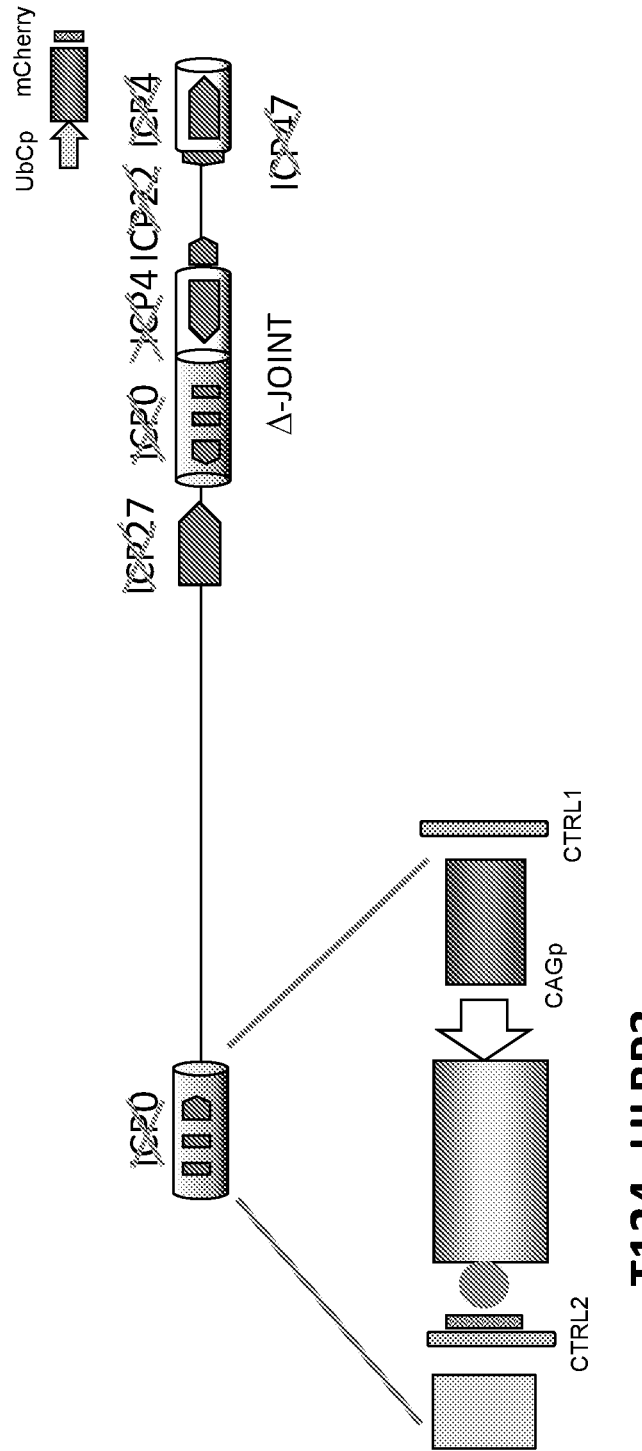
FIG. 11 shows a vector diagram of a recombinant HSV for delivering ULBP3 to a host cell.
Figure 13B:
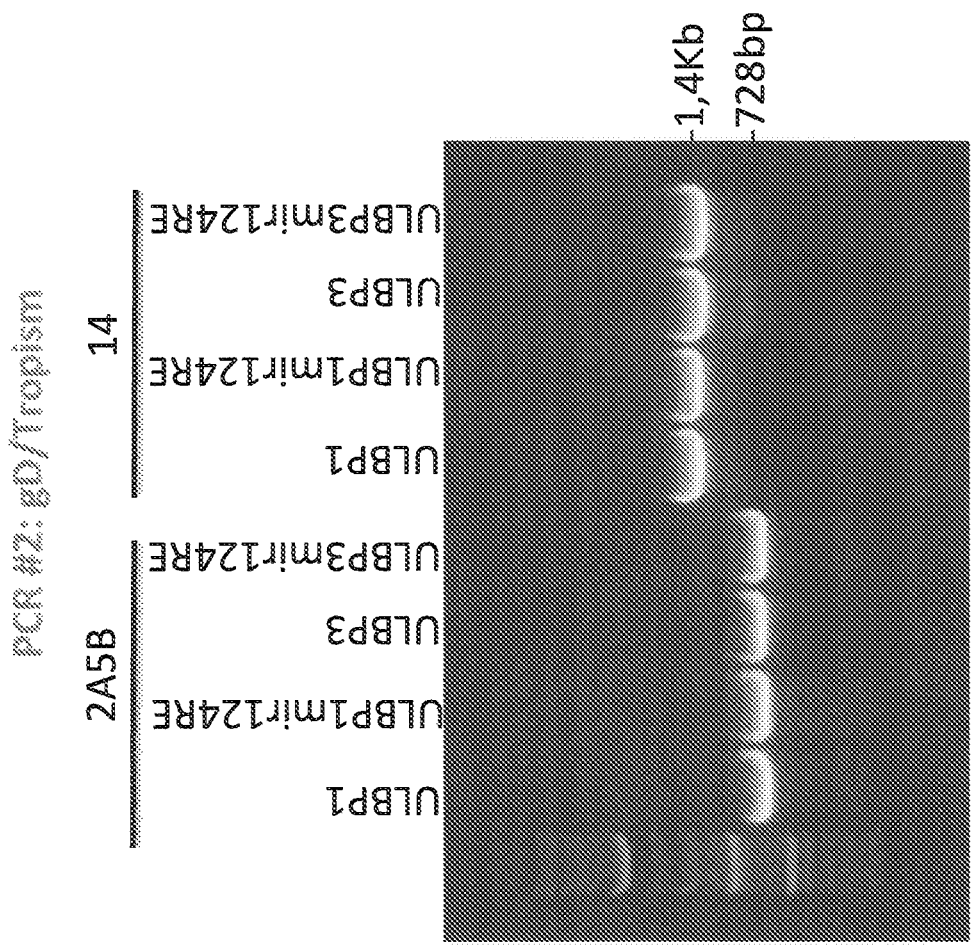
FIG. 13B shows PCR validation of gD/Tropism using primers gDF and gDR2 (PCR #2). Lanes represent BAC-DNA transfected in U2OS.
Figure 13A:
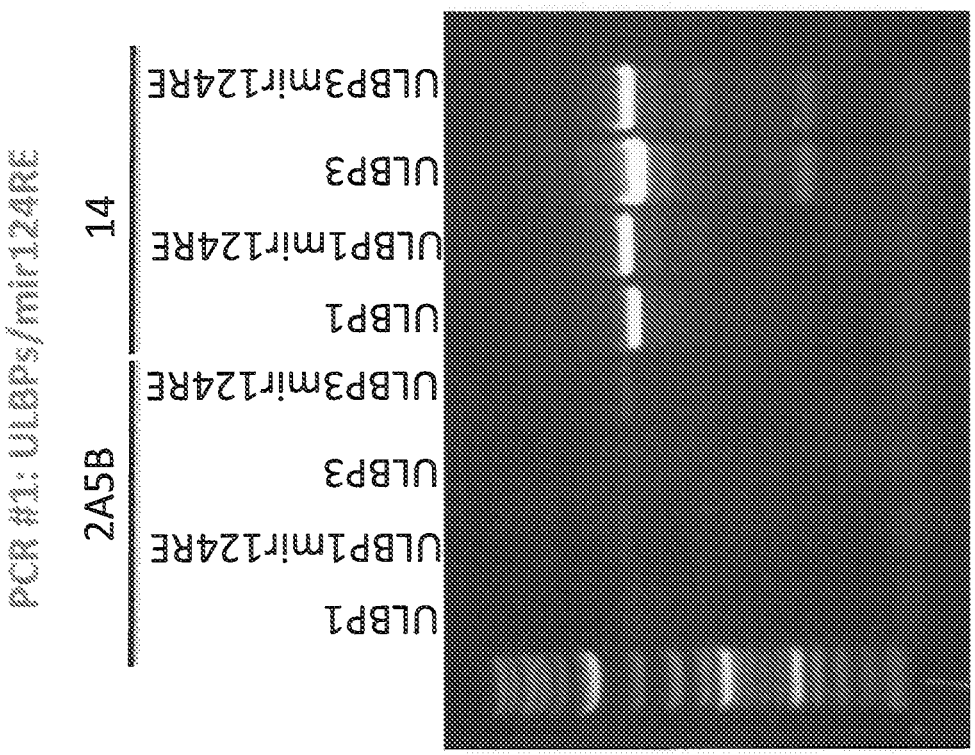
FIG. 13A shows PCR validation of mir124RE sequence recombination using primers: UL4f & pENTRcagULBPsf (PCR #1.
Figure 14:
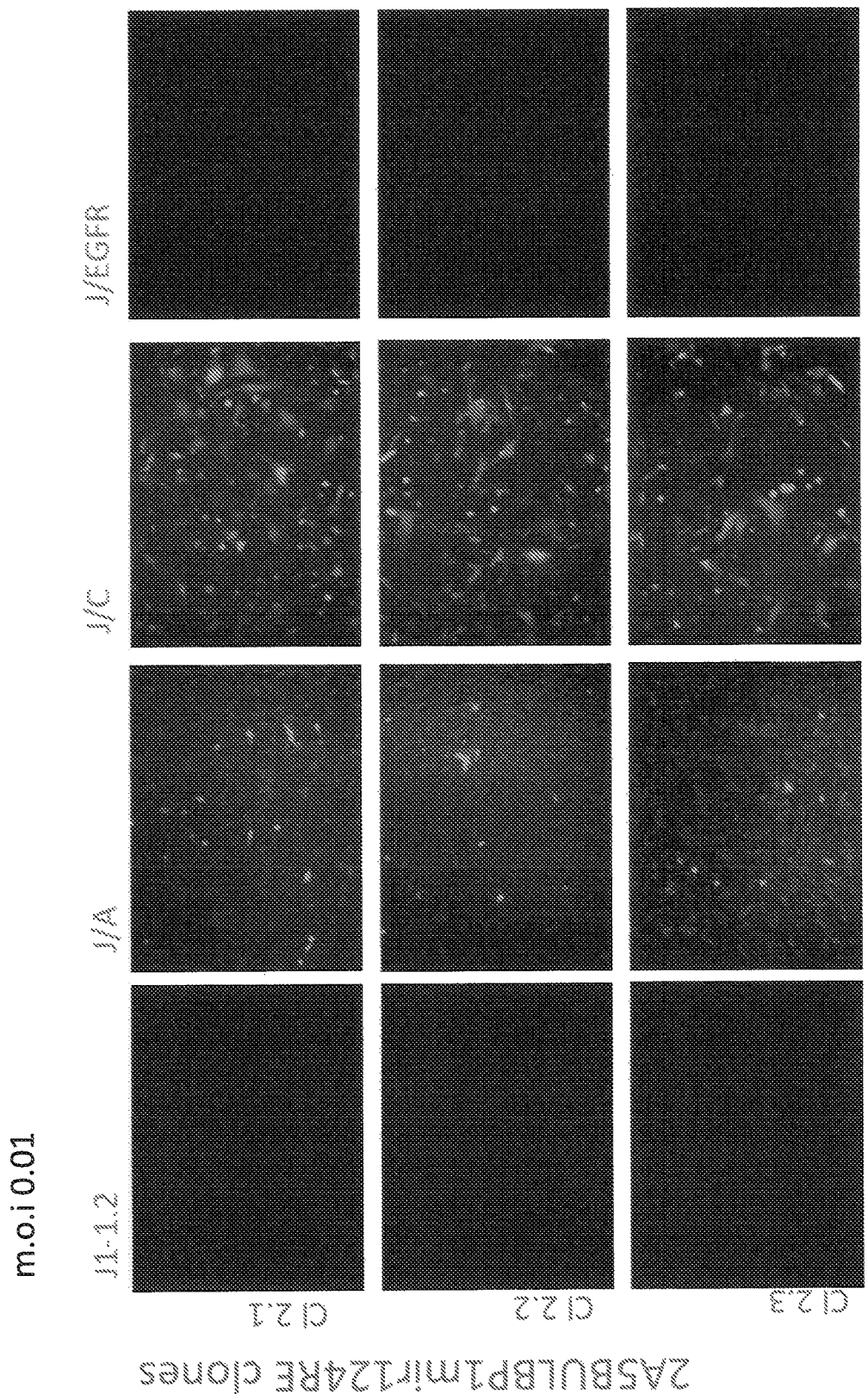
Figure 15:
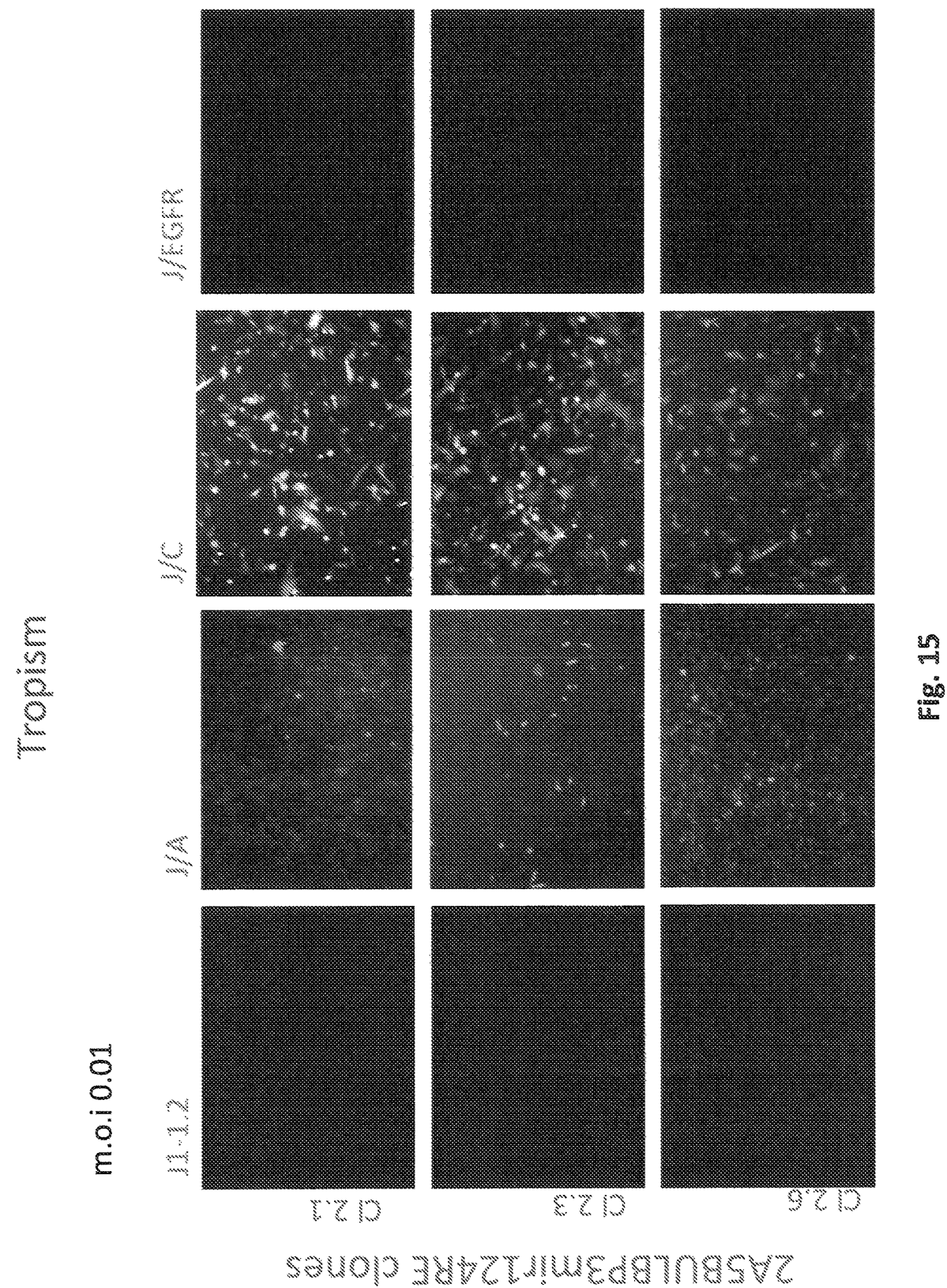
Figure 16:
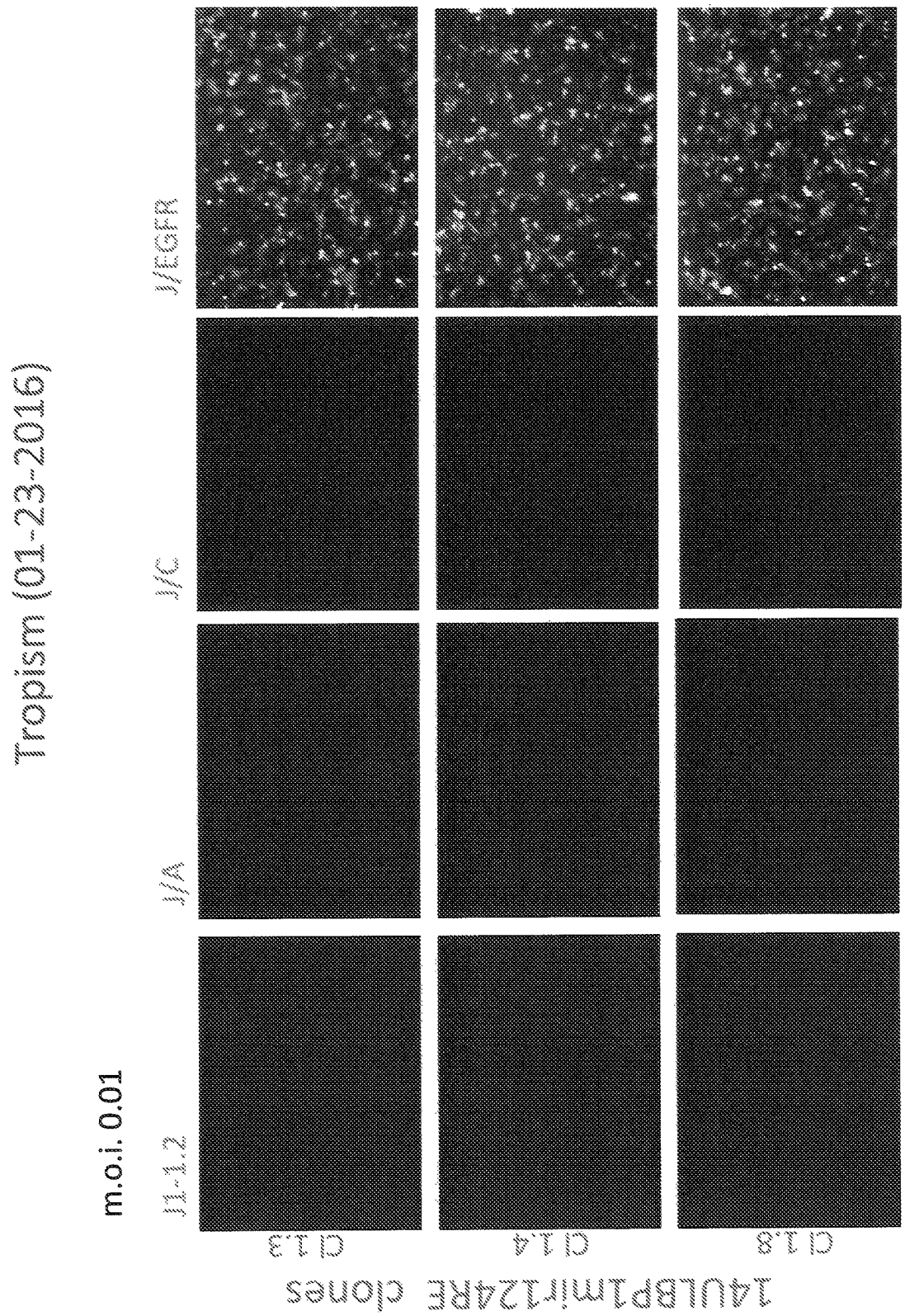
Figure 17:
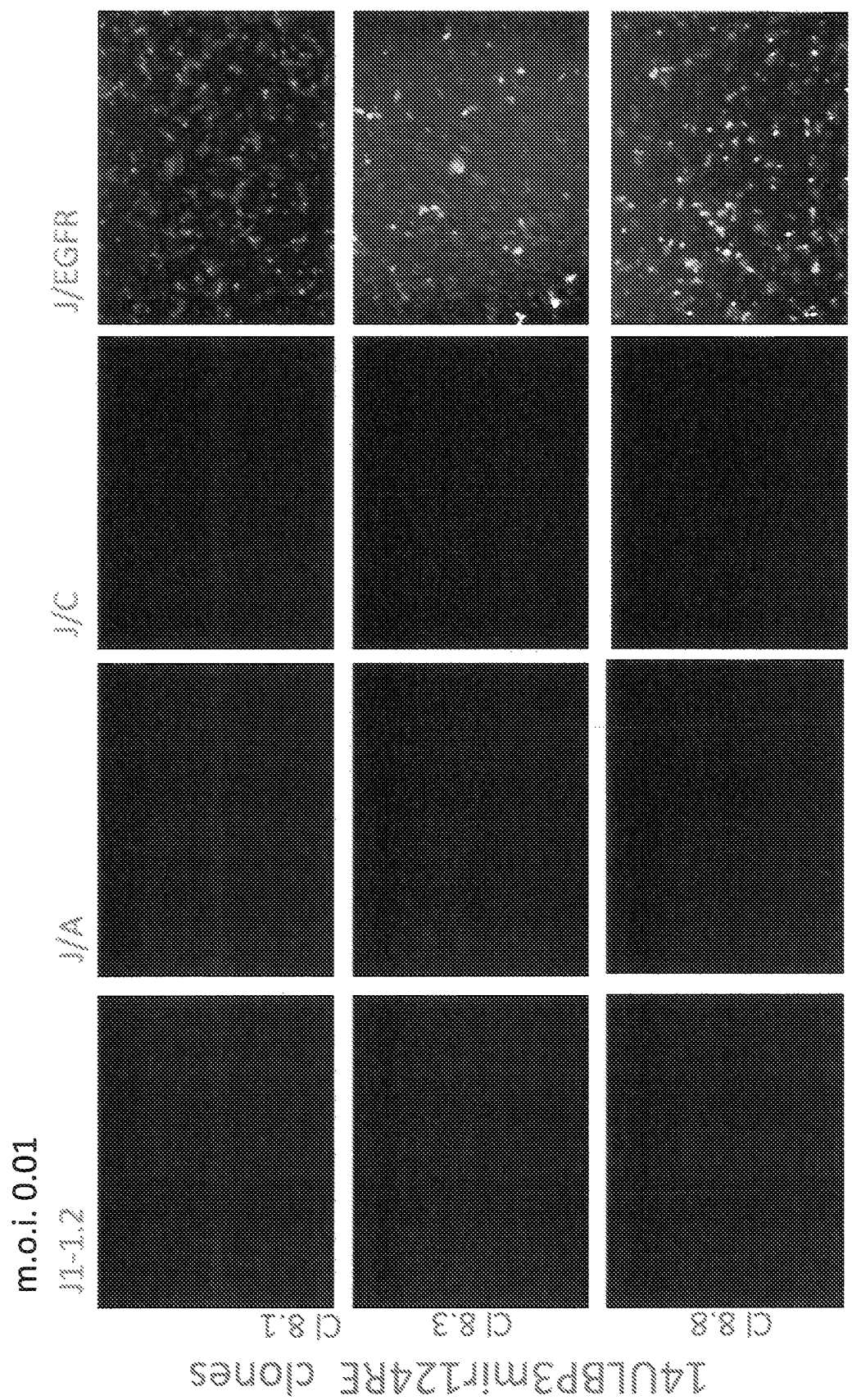

The results (FIG. 10A and FIG. 10B) reveal that miR124 inhibits ULBP1 and ULBP3 expression, suggesting that this approach can be used to block the proteins' expression in normal neurons.

Example 3

This example demonstrates that ULBP3 improves the therapeutic efficacy of HSV vector 2A5B.

As depicted in FIG. 20, an experiment was devised in which 30 Nude mice were divided into two 2 cohorts. Such mice lack T cells but possess NK cells and macrophages. One cohort (n=15) was treated every 4 days (throughout the experiment) with the Asialo GM1 Ab to deplete the NK cells from the mice; the other cohort (n=15) received the isotype control. All 30 animals were injected in the right flank with $10^6$ human glioma cells GBM30 expressing luciferase. Upon tumor formation, each cohort was divided into 3 groups, each receiving one of the following treatments: (1) single injection with the oncolytic HSV vector expressing ULBP3 (2A5B-ULBP3) ($2\times10^6$ pfu), (2) single injection with the unarmed HSV vector (2A5B) ($2\times10^6$ pfu) or (3) with PBS, as a negative control.

The results of this experiment are depicted in FIGS. 21, 22A, and 22B and in Table 3 below. In FIG. 21, the left panel demonstrates that NK cell activity enhances the benefit of oHSV therapy. Tumor growth curves of GBM30 flank tumor in (A) NK competent mice and (B) NK deficient mice treated with 2A5B, 2A5B-ULBP3, or PBS. Tumor size was assessed by measuring perpendicular diameters with a caliper. Differences in tumor growth were determined by ANOVA.

The data plotted in FIG. 22A reveal that, in the absence of NK cells, the 2A5BULBP3 oncolytic HSV vector exhibited a remarkably potent suppression of tumor growth when compared to the control backbone 2A5B vector, and even this 2A5B demonstrated efficacy in suppressing tumor growth over no treatment at all. The data plotted in FIG. 22B demonstrate an even more profound suppression in tumor growth for four of five animals (no measurable tumor size at all) when the 2A5BULBP3 oncolytic HSV was used in the presence of NK cells. As with FIG. 22A, some suppression of tumor grown was observed with the backbone 2A5B vector when compared to untreated (or sham-treated) animals. The single datum in FIG. 22B representing one of five animals for which tumor growth was observed among the cohort treated with the 2A5B-ULBP3 oncolytic HSV vector suggests it is an outlier.

In brief, the results indicate that four out of five animals treated with the 2A5B-ULBP3 oncolytic HSV vector showed a complete tumor regression with but a single dose. These results were unexpected and surprising. Moreover, ablation of NK cells decreased the therapeutic profile of the treatment. However, even in the absence of NK cells, ULBP3-expressing vectors demonstrated significant therapeutic benefit.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

TABLE 3

|  | Day 1-13 | Day 17 | Day 20 | Day 25 | Day 30 | Day 33 | Day 37 |
| --- | --- | --- | --- | --- | --- | --- | --- |
| NK Cells Present | | | | | | | |
| PBS vs 2A5B | ns | ns | ns | ****$p < 0.0001$ | ****$p < 0.0001$ | ****$p < 0.0001$ | ****$p < 0.0001$ |
| PBS vs 2A5B-ULBP3 | ns | ns | * $p = 0.033$ | ****$p < 0.0001$ | ****$p < 0.0001$ | ****$p < 0.0001$ | ****$p < 0.0001$ |
| 2A5B vs 2A5B-ULBP3 | ns | ns | ns | ns | ns | ns | ns |
| NK Depletion (Ab treatment) | | | | | | | |
| PBS vs 2A5B | ns | ns | ns | *** $p = 0.0007$ | ****$p < 0.0001$ | ****$p < 0.0001$ | ****$p < 0.0001$ |
| PBS vs 2A5B-ULBP3 | ns | * $p = 0.015$ | ** $p = 0.005$ | ****$p < 0.0001$ | ****$p < 0.0001$ | ****$p < 0.0001$ | ****$p < 0.0001$ |
| 2A5B vs 2A5B-ULBP3 | ns | ns | ns | ns | * $p = 0.024$ | ns $p = 0.073$ | ns $p = 0.063$ |

The invention claimed is:

1. A recombinant viral vector comprising an exogenous gene that expresses at least one NKG2D activating ligand protein,
   wherein the vector comprises one or more target sequences of miRNA,
   wherein the expression of the exogenous gene that expresses at least one NKG2D activating ligand protein is negatively regulated by the miRNA, wherein the miRNA is present at a greater concentration in non-cancerous cells compared to cancerous cells, and
   wherein the vector is selected from the group of viral vectors consisting of adenoviral vectors, adeno-associated viral vectors, and Herpes Simplex Virus (HSV) vectors.

2. The vector of claim 1, wherein the expression of the ligand protein sensitizes a cancer cell to NK-mediated cytotoxicity.

3. The vector of claim 1, wherein the NKG2D ligand protein is a UL16-Binding Protein (ULBP).

4. The vector of claim 3, wherein the NKG2D ligand protein is one or more ULBP selected from the group of ULBPs consisting of ULBP1, ULBP2, ULBP3, ULBP4, ULBP5, or ULBP6.

5. The vector of claim 3, wherein the NKG2D ligand protein has the amino acid sequence of one of ULBP1, ULBP2, ULBP3, ULBP4, ULBP 5, or ULBP6 or a protein having at least 95% identity to the amino acid sequence of one of ULBP1, ULBP2, ULBP3, ULBP4, ULBP5, or ULBP6.

6. The vector of claim 1, wherein vector expresses ULBP1, ULBP3, or both ULBP1 and ULBP3 when the vector is introduced into a cancer cell.

7. The vector of claim 1, wherein the vector comprises two or more miRNA target sequences, and optionally 3, 4, 5, or 6 target sequences, optionally in tandem, and optionally separated by spacers of four or more nucleotides.

8. The vector of claim 7, wherein the two or more miRNA target sequences comprise a reverse complement of the miRNA.

9. The vector of claim 1, wherein the miRNA comprises mir122, mir124, mir128, mir137, and/or mir199.

10. The vector of claim 1, wherein the miRNA target sequence or sequences are inserted into the 3'UTR of the exogenous gene that expresses the NKG2D ligand.

11. The vector of claim 1, further comprising one or more gene knockouts, knockdowns, deletions, insertions or other mutations that impair or block replication of the vector and/or expression of toxic genes.

12. The vector of claim 11, which is an HSV vector and wherein the one or more gene knockouts, knockdowns, deletions, insertions or other mutations are in one or more of the ICP0, ICP4, ICP22, ICP27 and ICP47, and optionally all of ICP0, ICP4, ICP22, ICP27 and ICP47.

13. The vector of claim 11, wherein the vector is replication incompetent in vivo.

14. The vector of claim 2, wherein the cell is a IDHmut cell.

15. The vector of claim 2, wherein the cell is a glioblastoma cell.

16. The vector of claim 1 wherein the vector is oncolytic.

17. The vector of claim 16, wherein the vector further comprises an exogenous gene encoding an oncolytic factor.

18. The vector of claim 17, wherein the oncolytic factor is one of a metalloproteinase, a prodrug-converting enzyme, a cytosine deaminase, a thymidine kinase, or a purine nucleoside phosphorylase.

19. The vector of claim 1, which comprises a transgene encoding matrix metalloproteinase 9 (MMP9).

20. The vector of claim 1, which comprises a transgene encoding an antibody against PD-L1.

21. The vector of claim 1, comprising transgenes encoding MMP9, one or both of ULBP1 and ULBP3, and optionally an antibody against PD-L1.

22. The vector of claim 21, wherein the transgene(s) encoding one or both of ULBP1 and ULBP3 is/are under the control of a miRNA.

23. The vector of claim 22, wherein the miRNA is mir124.

24. A nucleic acid encoding the vector of claim 1, wherein the nucleic acid is optionally a bacterial artificial chromosome (BAC).

25. A pharmaceutical composition comprising the vector of claim 1 and a pharmaceutically acceptable carrier.

26. A viral stock comprising the vector of claim 1.

27. A method for expressing a NKG2D ligand protein in a cancer cell, the method comprising administering the vector of claim 1 to a cancer cell under conditions sufficient for the vector to infect the cancer cell and to express the NKG2D ligand protein.

28. The method of claim 27, wherein the cancer cell is a glioblastoma cell.

29. A method of treating cancer in a mammalian subject having cancer, the method comprising administering an effective amount of the vector of claim 1, whereby the cancer is treated.

30. The method of claim 29, wherein the cancer is a glioma.

31. The method of claim 29 comprising administering the vector directly to the tumor.

32. The method of claim 31, wherein the administering is by intracranial injection.

33. The method of claim 29, wherein the subject is a human.

34. The vector of claim 1, wherein the miRNA target sequence or sequences are inserted into an essential gene of the vector.

35. The vector of claim 34, wherein the vector is an HSV vector and the essential gene is selected from ICP0, ICP4, ICP22, ICP27, and ICP47.

36. The vector of claim 1, wherein the expression of the gene encoding the at least one NKG2D activating ligand protein is placed under regulatory control of a promoter.

* * * * *